United States Patent
Matonick et al.

(10) Patent No.: US 9,999,759 B2
(45) Date of Patent: Jun. 19, 2018

(54) LINEAR STAPLERS HAVING RESORBABLE MICRONEEDLES CONTAINING ACTIVE AGENTS

(71) Applicant: Ethicon, Inc., Somerville, NJ (US)

(72) Inventors: John P. Matonick, Warren, NJ (US); Robert J. Tannhauser, Bridgewater, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 461 days.

(21) Appl. No.: 14/597,459

(22) Filed: Jan. 15, 2015

(65) Prior Publication Data
US 2016/0206864 A1   Jul. 21, 2016

(51) Int. Cl.
*A61M 37/00* (2006.01)
*A61B 17/072* (2006.01)
(Continued)

(52) U.S. Cl.
CPC ....... *A61M 37/0015* (2013.01); *A61B 17/072* (2013.01); *A61B 17/07207* (2013.01); *A61B 17/07292* (2013.01); *A61K 9/0021* (2013.01); *A61B 2017/00893* (2013.01); *A61B 2017/07271* (2013.01); *A61B 2017/07285* (2013.01);
(Continued)

(58) Field of Classification Search
CPC . A61B 17/068; A61B 17/1155; A61B 17/072; A61B 17/07207; A61B 17/07292; A61B 2017/00893; A61B 2017/07271; A61B 2017/07285; A61M 37/0015; A61M 1717/0682; A61M 2037/0046; A61M 2037/0061; A61K 9/0021
See application file for complete search history.

(56) References Cited

U.S. PATENT DOCUMENTS 5,275,323 A   1/1994 Schulze
6,273,897 B1  8/2001 Dalessandro et al.
(Continued)

FOREIGN PATENT DOCUMENTS

EP   1187653       3/2010
WO   WO 2006/049852  5/2006
(Continued)

OTHER PUBLICATIONS

US 8,152,042, 04/2012, Bettuchi et al. (withdrawn)
(Continued)

*Primary Examiner* — Lauren P Farrar
(74) *Attorney, Agent, or Firm* — David R. Crichton; Leo B. Kriksunov

(57) ABSTRACT

The present invention is directed to linear surgical staplers for joining tissue layers comprising a disposable cartridge installed in a first jaw connected to an opposing second jaw, said cartridge containing a plurality of deployable staples in arrays separated by a tissue resection slot and a plurality of resorbable medicant-releasing microneedles, said microneedles comprising elongated rods having a sharp tissue-penetrating distal end and a proximal end; said microneedles are releasably disposed on or within a tissue-facing surface of the cartridge, wherein the proximal end of the microneedles is supported on the cartridge. The present invention is also directed to methods of use of such stapler assembly devices.

18 Claims, 17 Drawing Sheets

(51) Int. Cl.
*A61K 9/00* (2006.01)
*A61B 17/00* (2006.01)

(52) U.S. Cl.
CPC .............. *A61M 2037/0046* (2013.01); *A61M 2037/0061* (2013.01)

(56) References Cited

U.S. PATENT DOCUMENTS

| | | | |
|---|---|---|---|
| 6,325,810 | B1 | 12/2001 | Hamilton et al. |
| 7,744,624 | B2 | 6/2010 | Bettuchi |
| 7,972,357 | B2 | 7/2011 | Bettuchi |
| 8,016,849 | B2 | 9/2011 | Wenchell |
| 8,096,458 | B2 | 1/2012 | Hessler |
| 8,241,308 | B2 | 8/2012 | Kortenbach et al. |
| 8,281,975 | B2 | 10/2012 | Criscuolo et al. |
| 8,366,677 | B2 | 2/2013 | Kaspar et al. |
| 8,657,176 | B2 | 2/2014 | Shelton, IV et al. |
| 2005/0184121 | A1* | 8/2005 | Heinrich ............ A61B 17/0686 227/175.1 |
| 2006/0108393 | A1 | 5/2006 | Heinrich et al. |
| 2007/0038181 | A1 | 2/2007 | Melamud et al. |
| 2009/0043250 | A1 | 2/2009 | Gonnelli |
| 2009/0062752 | A1 | 3/2009 | Gonnelli |
| 2011/0014181 | A1 | 1/2011 | Thornton |
| 2011/0147432 | A1 | 6/2011 | Heinrich et al. |
| 2012/0041412 | A1* | 2/2012 | Roth ..................... A61M 25/10 604/500 |
| 2012/0078189 | A1* | 3/2012 | Ogawa .............. A61M 37/0015 604/173 |
| 2012/0241503 | A1 | 9/2012 | Baxter, III et al. |
| 2012/0241505 | A1 | 9/2012 | Alexander, III et al. |
| 2013/0008937 | A1 | 1/2013 | Viola |
| 2013/0068819 | A1 | 3/2013 | Viola |
| 2013/0345671 | A1 | 12/2013 | Ryu et al. |
| 2015/0335872 | A1* | 11/2015 | Yang ................. A61M 37/0015 604/46 |
| 2016/0287668 | A1* | 10/2016 | Tankovich ........ A61M 37/0015 |

FOREIGN PATENT DOCUMENTS

| | | |
|---|---|---|
| WO | WO 2013/188884 | 12/2013 |
| WO | WO 2014/121051 | 8/2014 |
| WO | WO 2015/065625 | 5/2015 |

OTHER PUBLICATIONS

Jonsson, Kent, et al. "Breaking Strength of Small Intestinal Anastomoses", The American Journal of Surgery, vol. 145, Jun. 1983, pp. 800-803.

Yun Yang, Seung et al. "A Bio-Inspired Swellable Microneedle Adhesive for Mechanical Interlocking with Tissue", Nat Commun. vol. 4, 1702, Apr. 16, 2013, pp. 1-21.

Hong, Xiaoyun, et al, "Dissolving and Biodegradable Microneedle Technologies for Transdermal Sustained Delivery of Drug and Vaccine", Drug Design, Development and Therapy, vol. 2013, issue 7, pp. 945-952.

Yeu-Chun, Kim, et al. "Microneedles for Drug and Vaccine Delivery", Advanced Drug Delivery Reviews, vol. 64, 2012, pp. 1547-1568.

Yik-Hong, Ho, et al. "Techniques for Colorectal Anastomosis", World Journal Gastroenterol, Apr. 7, 2010, vol. 16, issue 13, pp. 1610-1621.

International Preliminary Report on Patentability re: PCT/US2016/013322 dated Jul. 18, 2017.

International Search Report re: PCT/US2016/013322 dated May 3, 2016.

* cited by examiner

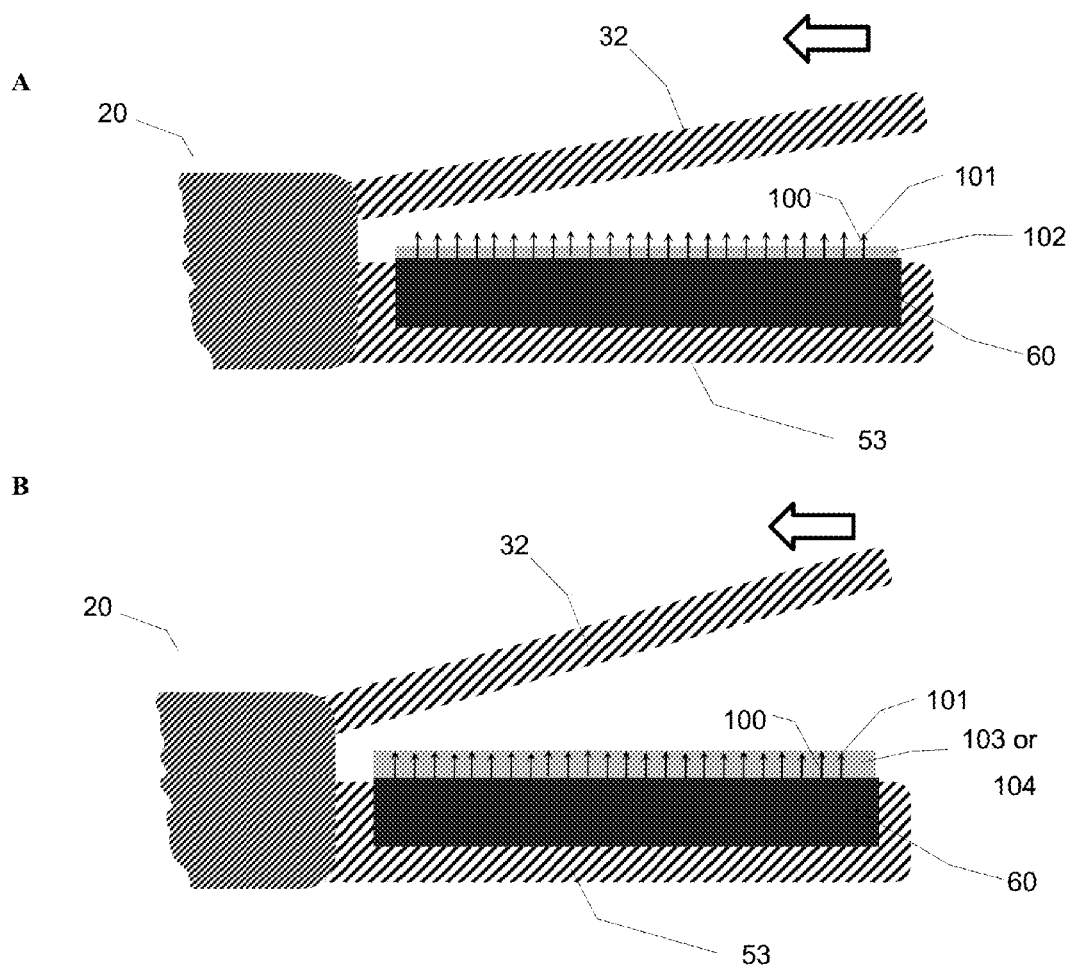

C

D

LINEAR STAPLERS HAVING RESORBABLE MICRONEEDLES CONTAINING ACTIVE AGENTS

FIELD OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Patent Application No. 2013/0068819 entitled "Structure Containing Wound Treatment Material", discloses an anvil assembly for a circular stapling apparatus, where the anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The wound treatment material is at least one of an adhesive, a sealant, a hemostat and a medicament.

U.S. Patent Applications Nos. 2011/0147432 and 2006/0108393, both entitled "Structure for applying sprayable wound treatment material", relate to surgical instruments, structures and methods for enhancing the properties of tissue to be repaired or joined and disclose a surgical stapling apparatus including a wound treatment material dispersion system for delivering wound treatment material to a target surgical site. The dispersion system includes an aperture formed in the anvil assembly oriented to dispense wound treatment material in an outward direction; and a source of wound treatment material in fluid communication with the aperture of the anvil assembly.

U.S. Patent Application No. 2011/0014181 entitled "Microneedle Delivery Device and Methods of Using Same" describes microneedle bioactive agent delivery systems, associated apparatus and methods of using such. The microneedles described are deliverable using a needle or syringe apparatus that can interface with existing medical devices or the devices can be used as standalone systems. The systems deliver at least one bioactive agent to a tissue in need thereof, for example, the myocardium.

U.S. Patent Application No. 2007/0038181 entitled "Method, system and device for delivering a substance to tissue" discloses devices and methods for delivering a substance to tissue or organs, particularly, the bladder, by a plurality of microneedles. The devices may include a delivery tube, a substance chamber to fill with the substance to be delivered, a plurality of needles, a plunger coupled to a handle movable relative to the tube to deliver the substance to the tissue through the needles, and a protective plate having at least one orifice therein, such that when the device is in a first, resting, position the needle tips are on a first side of the protective plate, and when the device is in a second, operational, position, the needles are on a second side of the protective plate.

U.S. Pat. No. 8,281,975, entitled "Surgical apparatus and structure for applying sprayable wound treatment material" discloses an apparatus for forming an anastomosis between adjacent sections of tissue. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

U.S. Pat. No. 8,152,042 entitled "Annular Adhesive Structure" discloses an apparatus for sealing at the anastomotic site. In some embodiments, a washer or structural body is wrapped completely around an anvil shaft, with staples driven through the structural body to release the sealant.

U.S. Pat. No. 7,972,357 entitled "Extraluminal sealant applicator and method" and U.S. Pat. No. 7,744,624 disclose apparatus for applying sealant to a target tissue of a surgical site. The apparatus includes a handle, a conduit and an end effector. The handle has means configured and adapted for operating the end effector and dispensing biological sealant to the surgical site via the end effector. The conduit stores and/or carries sealant towards the end effector. The end effector is configured to clamp around a body organ or tissue and apply and confine biological sealant in a substantially uniform manner. More specifically, the references disclose a system for applying sealant to a target tissue of a surgical site, comprising: a two-part sealant comprising a first part and a second part; an apparatus comprising: a handle; an end effector in operative association with the handle, the end effector including a first jaw member, a second jaw member, and a sealant-applying structure configured for applying sealant to the target tissue; the first jaw member being in fluid communication with a first conduit and a second conduit to convey sealant to the sealant-applying structure; the second jaw member being in fluid communication with a third conduit and a fourth conduit to convey sealant to the sealant-applying structure; the first and third conduits configured for conveying the first part of the two-part sealant to the sealant-applying structure; and the second and fourth conduits configured for conveying the second part of the two-part sealant to the sealant-applying structure.

U.S. Pat. No. 8,096,458 entitled "Pouch used to deliver medication when ruptured" describes a surgical stapling device, comprising: a handle portion; an elongate body portion; and a head portion located at the distal end of the body portion, the head portion including an anvil assembly, a staple cartridge assembly and a knife blade, the staple cartridge assembly having an annular array or group of staples, the anvil assembly being connected to the body portion along a shaft, the anvil assembly including: an anvil plate defining a plurality of staple forming pockets therein and a recess; and a wound treatment material disposed substantially within the recess.

U.S. Pat. No. 8,241,308 entitled "Tissue fastening devices and processes that promote tissue adhesion" discloses a fastener for fastening tissue segments having tissue surfaces, the fastener comprising: a first fastener member defining a fluid opening configured to receive a therapeutic agent, a plurality of fluid ports configured to deliver the therapeutic agent to the tissue segments, and a passageway between the fluid opening and the plurality of fluid ports; and a second fastener member having a substantially flat base and a post extending from the base proximate a center of the base, the post defining an opening for receiving and retaining the first fastener member such that the tissue segments to be fastened are retained between the first and second fastening members, the substantially flat base extending radially beyond a periphery of the post; wherein a longitudinal axis extends through the fluid opening, the fluid ports being radially arranged about the axis.

U.S. Pat. No. 8,366,677 "Microneedle arrays formed from polymer films" discloses a transdermal delivery device, comprising: a polymer base layer having microneedles projecting from a surface thereof, wherein the microneedles are compositionally homogenous with the polymer base layer, and wherein the microneedles of the transdermal delivery device are configured to be left in a skin surface of a subject to provide sustained delivery of an active agent even after removal of the polymer base layer, and wherein the polymer of the polymer base layer and the microneedles is polyvinyl alcohol.

U.S. Pat. No. 8,016,849 discloses a surgical apparatus, comprising: a first half-section having a distal end and a proximal end, the first half-section being adapted to receive a disposable loading unit in the distal end thereof; a second half-section in juxtaposed relation to the first half-section, the second half-section having a distal end and a proximal end; a disposable loading unit selectively operatively engageable with the distal end of the first half-section, the disposable loading unit including: a cartridge; a plurality of deployable needles supported within the cartridge, wherein each needle includes a lumen extending there through, and at least one hole formed in an outer periphery thereof for radially dispensing a fluid; a needle pusher in operative association with each needle for sequentially deploying each needle from the cartridge and into a target tissue; and an actuation member translatably disposed within the cartridge for delivering a driving force to each needle pusher to deploy the needles from the cartridge; and a wound treatment material applicator assembly for delivering a wound treatment material to the target surgical site, the applicator assembly including: a respective reservoir supported on an outer periphery of the distal end of each of the first and second half-sections, wherein the wound treatment material is disposed within each reservoir and at least one of the reservoirs is in direct fluid communication with the plurality of deployable needles.

U.S. Patent Publication No. 2005/0184121 discloses a surgical stapler comprising: a first jaw adapted to receive a staple cartridge in a distal end of the first jaw, the staple cartridge containing a plurality of individual surgical staples, and having a working surface with a plurality of staple slots formed therein; a second jaw having a staple anvil in a distal end of the second jaw, such that during the operation of the surgical stapler the staple cartridge and the staple anvil can be approximated relative to one another; a driving member for firing the surgical staples from their staple slots and against the approximated staple anvil; a body tissue property enhancing system for enhancing one or more properties of body tissue to be repaired or joined by the surgical stapler, the body tissue property enhancing system including: a biocompatible wound closure material dispensing system for dispensing an amount of surgically biocompatible wound closure material to a target staple site during at least one of prior to, after and concomitant with a firing of the surgical stapler to expel the plurality of staples loaded in the staple cartridge, the body tissue property enhancing system comprising at least one reservoir disposed in the staple cartridge for containing the biocompatible wound closure material therein; a plurality of ducts formed in the staple cartridge, wherein the plurality of ducts communicate with and extend from the at least one adhesive reservoir to the working surface of the staple cartridge; and a plurality of deployable needles each having a tip, the needles being adapted and disposed in the ducts of the staple cartridge such that their tips can be extended out of the working surface of the staple cartridge to penetrate at least a layer of the adjacent layers of body tissue and to allow the biocompatible wound closure material to be delivered along the exterior of the needles to penetrate one or more layers of the body tissue.

U.S. Patent Publication No. 2013/0008937 discloses a surgical stapling apparatus for joining body tissue, comprising: a staple anvil positioned at a distal end of the stapling apparatus and having a knife track defined therein; a staple cartridge positioned adjacent the staple anvil, the staple cartridge and staple anvil being juxtaposable relative to each other, the staple cartridge including a plurality of surgical staples individually disposed within individual staple slots formed in rows in the staple cartridge, and having a knife slot formed between adjacent rows of staples; a driving member for firing the surgical staples from the individual staple slots and against the staple anvil; a staple actuator having at least one cam wedge for ejecting staples and a knife blade, the staple actuator being movable along the staple rows; and a wound closure material applicator assembly operatively associated with the stapling apparatus, the assembly including: a conduit for conveying a wound closure material from a location external of the staple anvil and the staple cartridge to the staple actuator, wherein the conduit extends proximally from the staple actuator; and a distribution tip in communication with the conduit and having an orifice, the conduit and the distribution tip being attached to the staple actuator so that the conduit and the distribution tip move along the staple rows with the staple actuator.

Published PCT Patent Application No. WO2013/188884 discloses a wound closure device comprising one or more microstructure arrays, each comprising at least two microstructures. In some aspects, at least one microstructure is capable of penetrating into tissue and holding it in place. In some aspects, the microstructures are microneedles.

Published European Patent Application No. EP 1,187,653 discloses a device for transport of a material across or into a biological barrier comprising a) a plurality of hollow microneedles each having a base end and a tip, with at least one hollow pathway disposed at or between the base end and the tip, b) a substrate to which the base ends of the microneedles are attached or integrated, and c) at least one reservoir which is in connection with the base ends of at least one of the microneedles, either integrally or separably until the moment of use, wherein the volume or amount of material to be transported can selectively be altered.

U.S. Patent Publication No. 2009/0043250 discloses membrane containing microneedles, microneedle arrays, and needles.

U.S. Patent Publication No. 2009/0062752 discloses a microneedle device, comprising a first layer formed into the shape of a microneedle and comprising a material suitable for piercing tissue, and a second layer having a switch formed thereon and capable of being coupled into electrical communication with microneedle.

U.S. Patent Publication No. 2013/0345671 discloses a drug delivery device for attachment to the outer wall of a blood vessel, the blood delivery device comprising: a) a body made of a biocompatible material and formed so as to cover the blood vessel; b) one or more needles made of a biocompatible material, which are connected to the inside of the body and inserted into the tunica media of the blood vessel so as to deliver a drug to vascular smooth muscle cells; c) one or more drug reservoirs formed in the body; and d) microchannels formed in the needles and serving to deliver the drug from the drug reservoirs to the tunica media of the blood vessel.

An article titled "Dissolving and biodegradable microneedle technologies for transdermal sustained delivery of drug and vaccine" by Xiaoyun Hong et al., Drug Design, Development and Therapy 2013:7, pp. 945-95, provides an overview of microneedle technology, disclosing that dissolving and biodegradable microneedle technologies have been used for transdermal sustained deliveries of different drugs and vaccines. The review describes microneedle geometry and the representative dissolving and biodegradable microneedle delivery methods via the skin, followed by the fabricating methods.

An article titled "A Bio-Inspired Swellable Microneedle Adhesive for Mechanical Interlocking with Tissue", by Seung Yun Yang et al., Nat Commun. 2013, 4, p. 1702 discloses a biphasic microneedle array that mechanically interlocks with tissue through swellable microneedle tips, achieving increase in adhesion strength compared to staples in skin graft fixation, and removal force of about 4.5 N/cm2 from intestinal mucosal tissue and comprising a poly(styrene)-block-poly(acrylic acid) swellable tip and non-swellable polystyrene core, conical microneedles penetrate tissue with minimal insertion force and depth, yet high adhesion strength in their swollen state.

An article titled "Microneedles for drug and vaccine delivery" by Yeu-Chun Kim et al., Adv Drug Deliv Rev. 2012, 64(14), pp. 1547-1568, provides an overview of microneedle technology, disclosing that microfabrication technology enabled microneedle manufacture as (i) solid microneedles for skin pretreatment to increase skin permeability, (ii) microneedles coated with drug that dissolves off in the skin, (iii) polymer microneedles that encapsulate drug and fully dissolve in the skin and (iv) hollow microneedles for drug infusion into the skin. Microneedles have been used to deliver a broad range of different low molecular weight drugs, biotherapeutics and vaccines, including published human studies with a number of small-molecule and protein drugs and vaccines. Influenza vaccination using a hollow microneedle is in widespread clinical use and a number of solid microneedle products are sold for cosmetic purposes. In addition to applications in the skin, microneedles have also been adapted for delivery of bioactives into the eye and into cells.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult. Other technologies attempt to deliver the materials upon deploying of the stapler, resulting in complex equipment which delivers materials into highly compressed tissue. There is a need in improving delivery of therapeutic agents to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site, especially when sealing an anastomosis between adjacent intestinal sections so as to improve tissue viability and to prevent leakage. The present invention, in one embodiment, relates to a linear surgical stapler for joining tissue layers having a disposable cartridge installed in a first jaw connected to an opposing second jaw and a plurality of resorbable medicant-releasing microneedles. The microneedles are elongated rods having a sharp tissue-penetrating distal end and a proximal end and releasably disposed on or within a tissue-facing surface of the cartridge, wherein the proximal end of each microneedle is supported on the cartridge. The cartridge contains a plurality of deployable staples positioned in arrays that are separated by a tissue resection slot. The microneedles are preferably positioned on a periphery of the cartridge outside of the arrays of the staples and distally to the tissue resection slot. The microneedles can further comprise a barb at the distal end thereof and positioned substantially perpendicular to the tissue-facing surface. The cartridge preferably has at least 10 microneedles that are from 50 microns to about 1000 microns in diameter and from about 100 microns to about 2500 microns long.

In one embodiment, the microneedles are releasably supported by an attachment strip disposed on the tissue-facing surface. The attachment strip can be compressible foam layer in which the microneedles have been embedded. In another embodiment, the microneedles are supported by a buttress or a tissue thickness compensator that is releasably disposed on the tissue-facing surface. In all of the foregoing embodiments, the microneedles are configured to be left in the tissue layers after joining of the tissue layers.

The medicant provided by the microneedles can be a drug, an enzyme, a growth factor, an anti-inflammatory agent, a vasodilating agent, a peptide, a protein, a nutrient, an excipient, a cell, or combinations thereof. The medicant can be released from the microneedle into the adjacent tissue over a period of from about 2 hours to about 4 weeks, more preferably from about 4 hours to about 5 days, most preferably from about 4 hours to about 3 days.

The present invention, in another embodiment, relates to methods of joining tissue layers by disposing a plurality of soluble or resorbable microneedles containing at least one medicant on a disposable cartridge installed in a first jaw connected to an opposing second jaw of a linear stapler, said cartridge containing a plurality of deployable staples in arrays separated by a tissue resection slot; said microneedles comprising elongated rods having a tissue-penetrating distal end and a proximal end, releasably disposed on or within a tissue-facing surface of the cartridge, wherein the proximal end of the microneedles is supported on the cartridge; positioning the tissue layers between the first jaw connected and the second jaw; bringing the first jaw connected and the second jaw together thus compressing the tissue layers between said jaws; thus deploying said microneedles into said tissue layers; simultaneously or consecutively deploying the plurality of staples into the tissue layers thus closing or joining the tissue layers; opening the jaws and removing the linear stapler with the cartridge from contact with the tissue layers, allowing the microneedles to stay in the tissue layers; and allowing the medicant to be released into the tissue layers from the microneedles. The microneedles are preferably positioned on a periphery of the cartridge outside of the arrays of the staples and distally to the tissue resection slot. The microneedles can further have a barb at the distal end thereof that are positioned substantially perpendicular to the tissue-facing surface. The microneedles can, in one embodiment, be releasably supported by an attachment strip disposed on the tissue-facing surface. The attachment strip can be a compressible foam layer in which the microneedles have been embedded. The microneedles can, in another embodiment, be supported by a buttress or a tissue thickness compensator that is releasably disposed on the tissue-facing surface. The microneedles are configured to separate from the cartridge upon opening of the jaws and removing the linear stapler with the cartridge from contact with the tissue layers, so that the microneedles remain in the tissue layers after joining of the tissue layers, in which the microneedles fully dissolve or are resorbed within the tissue layers over time. The microneedles can contain or include a drug, an enzyme, a growth factor, an anti-inflammatory agent, a vasodilating agent, a peptide, a protein, a nutrient, an excipient, a cell, or combinations thereof as the medicant. The medicant can be released over a period of from about 2 hours to about 4 weeks, more preferably from about 4 hours to about 5 days, most preferably from about 4 hours to about 3 days.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-op leakage of the anastomosis has been shown to lead to morbidity and mortality.

Typical surgical stapling instruments, such as surgical linear stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component. For linear surgical staplers, a disposable stapling cartridge is the staple-containing component, the cartridge typically installed in a jaw of the device, such as in a lower jaw adapted to hold the cartridge, and the opposing or upper jaw is the anvil component.

Figure 1:
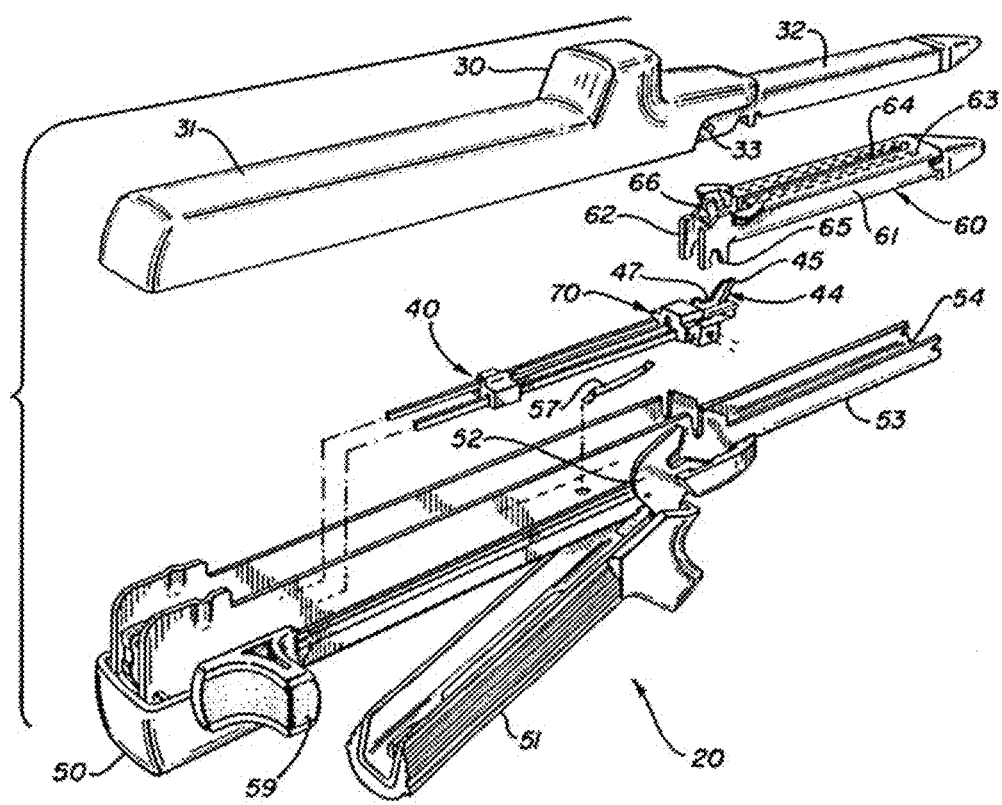
FIG. 1 shows prospective view of a linear surgical stapling instrument or linear stapling device.

Referring now to FIG. 1, a generic linear surgical stapling instrument or linear stapling device is shown, with the figure taken from the U.S. Pat. No. 5,275,323 "Surgical stapler", assigned to Ethicon, Inc., Somerville, N.J., and incorporated herein by reference in its entirety for all purposes.

A typical linear surgical stapler applies into the tissue a plurality of rows of staples that are housed in a disposable cartridge. The cartridge has a slot disposed between adjacent, parallel rows of staples and extending substantially the entire length of the rows of staples. The stapler includes firing means for the staples and a cutting means that is movable along the slot. As seen in FIG. 1, a typical surgical stapler 20 comprises an upper piece 30, a firing means 40, a lower piece 50 and a staple cartridge 60.

Staple cartridge 60 fits within the lower piece 50. Specifically, the front part of staple cartridge 60 fits into lower jaw channel 54. More specifically, the parallel side walls 61 of the staple cartridge 60 fit within the lower jaw channel 54. The back part of staple cartridge 60 has a breakable transverse member 66. This breakable transverse member 66 is placed on top of cartridge locking means 47 of firing means 40. At the same time two legs 65 within rearwardly extending surfaces 62 secure staple cartridge 60 to lower piece 50.

In FIG. 1, upper piece 30 has a rear upper handle portion 31 and a front upper jaw portion 32. Likewise, lower piece 50 includes a rear movable lower handle portion 51 and a front lower jaw portion 53. The embodiment of the surgical stapler as illustrated in FIG. 1 incorporates firing means 40, leaf spring 57, and staple cartridge 60 into lower piece 50. Yet, these elements may be placed in upper piece 30 instead of lower piece 50.

Lower handle portion 51 illustrated in FIG. 1 is movable, more specifically, pivotable between two locking positions. In the first locking position, movable lower handle portion 51 is positioned at an oblique angle to lower jaw portion 53. During the first locking position a C-shaped member 52 of lower handle 51 is disengaged from a stationary locking pin 33. The upper and lower pieces, 30 and 50, respectively may be separated before or after operation of stapler 20 in the first locking position. On the other hand, in the second locking position the C-shaped member 52 of movable lower handle 51 locks the upper and lower pieces 30 and 50 together. In the second locking position the movable lower handle portion 51 is parallel to lower jaw portion 52. This second locking position occurs by engaging stationary locking pin 33 with C-shaped member 52. This movable handle portion design may be on the upper or lower handle portions, 31 and 51, respectively.

Firing knob 59 activates firing means 40. Firing means 40 also includes a roof assembly 70 and also contains a cutting means such as a knife blade assembly 44. A cutting surface 45 is included in knife blade assembly 44. Although a knife blade assembly is illustrated in FIG. 1, tissue may be cut in many ways besides knife or razor blade cutting.

When knife blade assembly 44 is in alignment with slot 64, firing knob 59 is manually pushed towards staple cartridge 60. Pushing firing knob 59 moves knife blade assembly 44 forward toward the staple cartridge 60. Then knife cutting surface 45 is moved through slot 64 of staple cartridge 60 simultaneously advancing staples from staple cartridge 60 through longitudinal slots 63. In some staple cartridge 60 embodiments, knife blade assembly is incorporated into the staple cartridge 60.

Other versions and modifications of the linear surgical stapler are known to a skilled artisan, all including a staple cartridge 60 having a plurality of longitudinal slots 63 containing staples (staples are not shown in FIG. 1), longitudinal slots 63 arranged in several rows on both sides of the slot 64. There are typically at least two and frequently at least three rows of longitudinal slots 63 on each side of the slot 64, with slots 64 in each row typically staggered or offset relative to the slots in the adjacent row, to improve the sealing and prevent leakage along the stapling line.

According to the present invention, application of therapeutic material or medically useful agents or medicants to tissue layers is performed via insertion into the tissue, including insertion into subserosal tissue, of soluble or resorbable microneedles containing the medicants. The insertion of the microneedles containing the medicants into the tissue is performed immediately before the joining of the tissue by staples (i.e. before deploying of the staples into the tissue), or simultaneously and synchronously with the joining of the tissue by staples, and is performed by using the same surgical stapler that deploys the staples. The medicants are then released from soluble or resorbable microneedles into the surrounding tissue over time, such time ranging from a few hours to several days to several weeks, such as 12 hours, 24 hours, 48 hours, 1 week, 2 weeks, 4 weeks, with such medicant release referred to as sustained release of medicants. Time of medicant release is generally not longer than about 4 weeks. The soluble or resorbable microneedles will fully dissolve or fully resorb over a period of microneedle resorption, which can be same as the time of medicant release, or longer than the time of medicant release, such as 24 hours, 48 hours, 1 week, 2 weeks, 4 weeks, 6 weeks, but in general not longer than about 6-8 weeks.

Therapeutic material or therapeutic agent or medicant refers to any medically useful substance or combination of substances, which can improve tissue viability, including drugs, enzymes, growth factors, peptides, proteins, nutrients, excipients, antimicrobial agents, and any other injectable pharmaceutical agents. Of particular interest are medicants such as growth factors, vasodilators, and antithrombotic agents. Other examples of therapeutic agents are also autologous cells and fibrinogen.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jönsson, H. Jiborn, B. Zederfeldt, "Breaking strength of small intestinal anastomoses", The American Journal of Surgery, v. 145, pp. 800-803, 1983;

Y.-H. Ho, M. A. T. Ashour, "Techniques for colorectal anastomosis", World Journal of Gastroenterology, 16(13), pp. 1610-1621, 2010.

According to the present invention, the tissue is treated with medicants outside of the staple line, not within the staple line, in order to improve the outcomes for the stapled tissue recovery. The present invention discloses embodiments of surgical staplers delivering soluble or resorbable microneedles outside of the staple line, with the microneedles impregnated and/or coated with the medicants, with the microneedles delivered immediately before or simultaneously with the stapling and left in the tissue to release the active agents or medicants. The microneedles are injected/inserted into tissue by the action of the stapler, preferably the microneedles are inserted into both layers of tissue being stapled together. The microneedles are left in the tissue for immediate and/or delayed or sustained release of medicants, and the microneedles eventually fully dissolve or resorb within the tissue.

Figure 2:
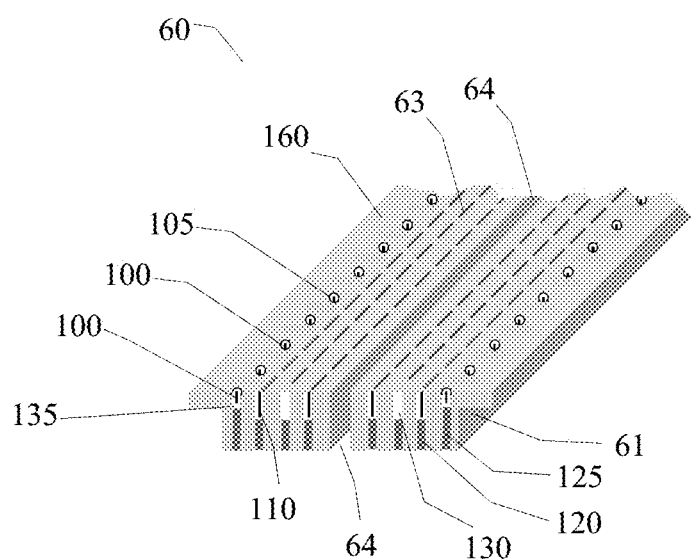
FIG. 2 shows schematic prospective cutout view of an embodiment of the staple cartridge of the present invention.

According to the present invention, the staple cartridge of the linear surgical stapler has a plurality of solid, optionally barbed implantable microneedles which are inserted into the tissue by the action of the stapler. Referring now to FIG. 2, one embodiment of staple cartridge 60 is shown in a schematic cutout view, staple cartridge 60 having tissue facing surface 160, parallel side walls 61, with slot 64 separating several staggered rows of longitudinal slots 63 within tissue facing surface 160 on each side of slot 64. Longitudinal channels 130 are in communication with longitudinal slots 63 and contain staples 110 and staple advancers 120, with the staples 110 configured to advance through longitudinal slots 63 into the tissue when pushed by staple advancers 120.

A plurality of soluble or resorbable microneedles containing the medicants, designated as microneedles 100, are arranged in an elongated microneedle array parallel to longitudinal slots 63. Microneedles 100 are disposed in microneedle channels 135; microneedles 100 are advanced into the tissue by microneedle advancers 125 with microneedles 100 exiting staple cartridge 60 via microneedle openings or microneedle wells 105.

Microneedles 100 are positioned on a periphery of the staple cartridge 60, outside of the staple line (or staple arrays) and distally to the tissue resection line, which corresponds to slot 64 or tissue resection slot.

In operation of the embodiment shown in FIG. 2, microneedles 100 are inserted into the tissue simultaneously with the staples, by the action of firing knob 59 which activates firing means 40 shown in FIG. 1 and simultaneously acts on staple advancers 120 and microneedle advancers 125. Microneedles 100 are in alignment with staples 110 and substantially perpendicular to tissue facing surface 160.

Figure 3:
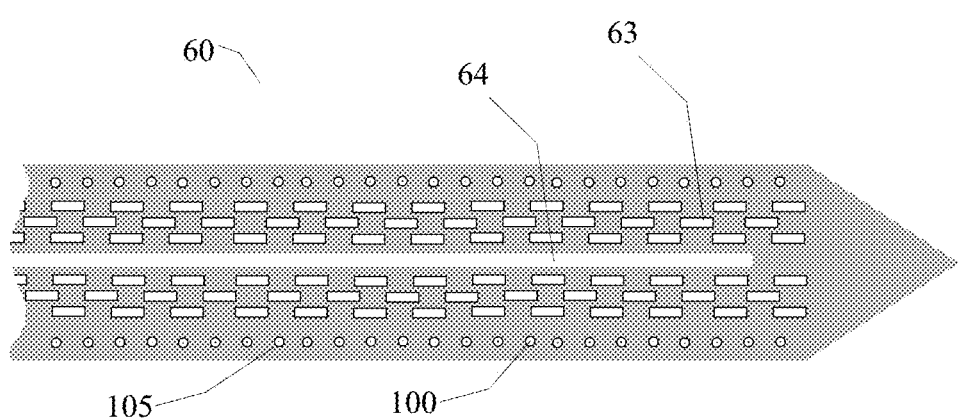
FIG. 3 shows schematic top view of an embodiment of the staple cartridge of the present invention.

FIG. 3 shows schematic top view of the staple cartridge 60 of the embodiment of FIG. 2. In the embodiment of the linear stapler cartridge shown in FIGS. 2-3, microneedles are deployed in wells similar to the staples wells and pushed into the tissue by the same mechanism as the staples. This embodiment requires modification of the currently used stapling cartridges to add rows of microneedle filled wells. Alternatively, one of the rows containing staples can be replaced with a row containing microneedles. Microneedles are deployed similarly to staples and simultaneously with the staples by the same mechanism. Preferably microneedles are in a form of elongated pins with sharp barbed tips. Alternatively, microneedles can be in a form of a "U"-shape, similar to the staple, but with legs shorter relative to the metal staples.

Figure 4:
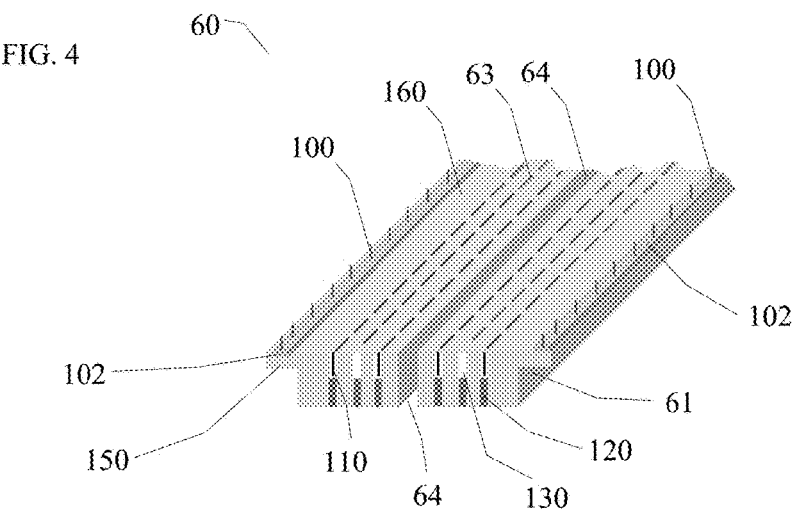
FIG. 4 shows schematic cutout view of an embodiment of the staple cartridge of the present invention

Referring now to FIG. 4, an alternative embodiment of staple cartridge 60 is shown in a schematic cutout view, with microneedles 100 disposed on tissue facing surface 160, optionally on a lateral extension 150 of tissue facing surface 160. A plurality of microneedles 100 are arranged in an elongated array on a periphery of staple cartridge 60, with microneedle array parallel to longitudinal slots 63 and distal from slot 64, outside of the staple lines corresponding to longitudinal slots 63.

Microneedles 100 are removably attached to tissue facing surface 160 by attachment strip 102. Attachment strip 102 is an elongated flat supporting structure disposed on tissue facing surface 160 and running along the length of staple cartridge 60 parallel to longitudinal slots 63 and distally from slot 64, outside of the staple lines corresponding to longitudinal slots 63. There is at least one attachment strip 102 on one side of staple cartridge 60. As shown, preferably there are two attachment strips 102 on each side of staple cartridge 60, outside of the staple lines corresponding to longitudinal slots 63 and distal from slot 64.

Figure 5:
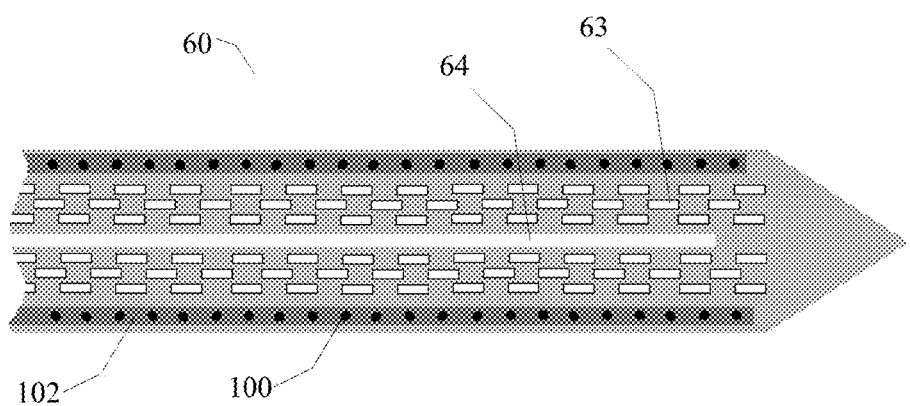
FIG. 5 shows schematic top view of an embodiment of the staple cartridge of the present invention.

FIG. 5 shows a schematic top view of staple cartridge 60 of the embodiment of FIG. 4.

Figure 6:
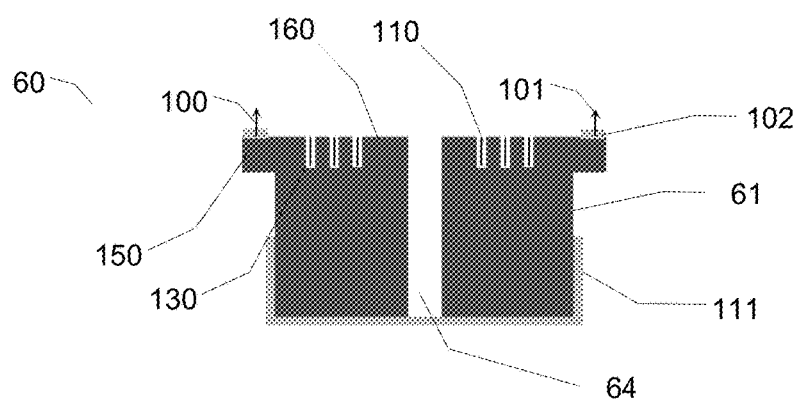
FIG. 6 shows schematic cross-sectional front view of an embodiment of the staple cartridge of the present invention.

FIG. 6 shows a schematic cross-sectional front view of staple cartridge 60 of the embodiments of FIGS. 4-5, with longitudinal slots 63, staple advancers 120, and other aspects of staple 110 delivery not shown for simplicity. Microneedles 100 with optional barbs 101 at the sharp ends and distal to tissue facing surface 160 are supported on tissue facing surface 160, optionally, as shown, on lateral extension 150 of tissue facing surface 160, by attachment strip 102. Also shown in FIG. 6 is a rear cover 111, which was not shown in FIGS. 2-5. Microneedles 100 can be in alignment with staples 110 and substantially perpendicular to tissue facing surface 160.

Figure 7:
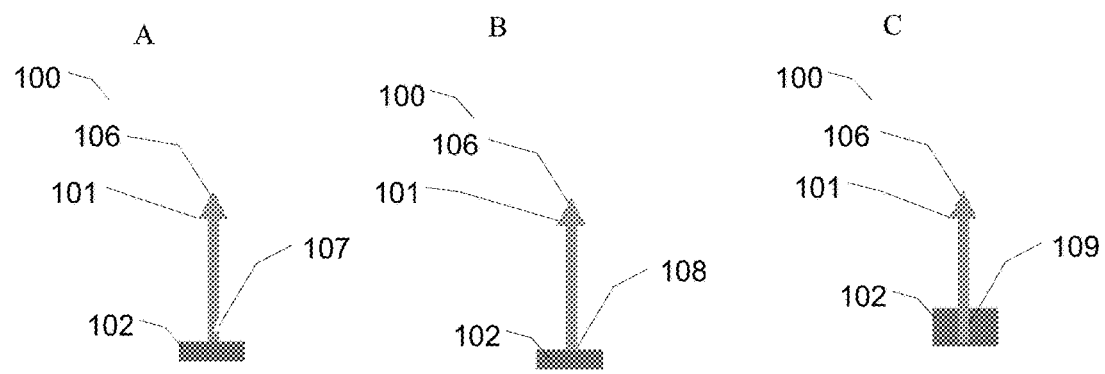
FIG. 7 shows schematic cross-sectional front view of microneedles embodiments of the present invention.

Microneedles 100 are detachably supported on attachment strip 102, so that upon insertion into tissue, microneedles 100 break off or detach from attachment strip 102 and stay in the tissue. Microneedles can have a sharpened tip facing the tissue. Referring now to FIG. 7, several different aspects of microneedles 100 supported on attachment strip 102 are shown. FIG. 7A shows microneedle 100 with sharp tip 106 and optional barb 101 strongly attached to attachment strip 102 at the end opposite the barb 101, with a nick or detent 107 weakening microneedle 100 in the vicinity of microneedle attachment to attachment strip 102. Advantageously, after insertion of microneedle 100 into the tissue and engagement of the barb 101 with the tissue, microneedle 100 breaks off at the nick or detent 107 as staple cartridge 60 is removed, with microneedle 100 staying in the tissue. Strong attachment of microneedle 100 having detent 107 is performed by adhesives, co-molding, welding, and other methods known to these skilled in the art.

FIG. 7B shows microneedle 100 with sharp tip 106 with optional barb 101 detachably attached to attachment strip 102 at the end opposite the barb 101. The detachability of microneedle 100 from strip 102 is achieved by weak joining of microneedle 100 to strip 102 by adhesives, welding, and other methods known to these skilled in the art in the area 108 between the end of the microneedle 100 opposite the barb 101 and the attachment strip 102. Advantageously, after insertion of microneedle 100 into the tissue and engagement of the barb 101 with the tissue, microneedle 100 separates from attachment strip 102 in the area 108 as staple cartridge 60 is removed, with microneedle 100 staying in the tissue.

FIG. 7C shows microneedle 100 with sharp tip 106 and with optional barb 101, detachably attached to attachment strip 102 at the end opposite the barb 101, with detachability achieved by a weak joint formed by a snug insertion of microneedle 100 into a cavity or aperture 109 in attachment strip 102, or direct insertion of microneedle 100 into the attachment strip 102 which can be made of a pierceable material, such as a foam or a gel. Advantageously, after insertion of microneedle 100 into the tissue and engagement of the barb 101 with the tissue, microneedle 100 separates from attachment strip 102 as staple cartridge 60 is removed, with microneedle 100 staying in the tissue.

Figure 8:
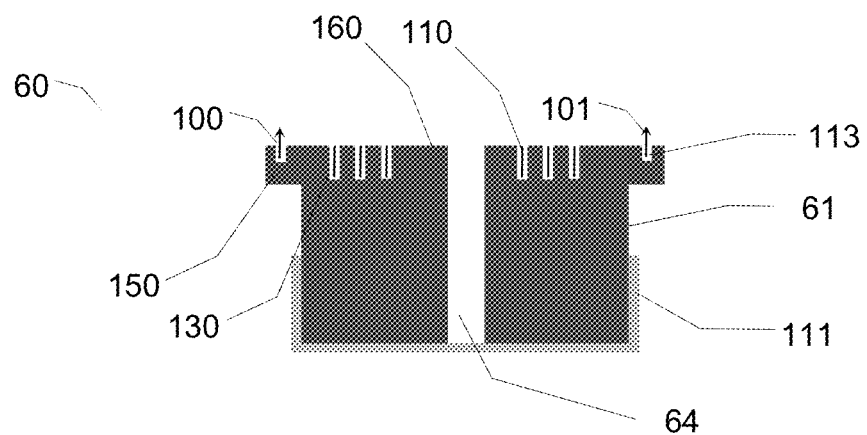
FIG. 8 shows schematic cross-sectional front view of an embodiment of the staple cartridge of the present invention.

In the embodiment shown in FIG. 8, microneedle 100 with barb 101 is detachably attached directly to staple cartridge 60 at the end opposite the barb 101, without any attachment strip 102, with detachability achieved by a joint formed by a snug, frictional fit insertion of microneedle 100 into a cavity 113 in tissue facing surface 160, or optionally, as shown, cavity 113 in lateral extension 150 of tissue facing surface 160. Advantageously, after insertion of microneedle 100 into the tissue and engagement of the barb 101 with the tissue, microneedle 100 separates from staple cartridge 60 as staple cartridge 60 is removed, with microneedle 100 staying in the tissue. Longitudinal slots 63, staple advancers 120, and other aspects of staple 110 delivery are not shown for simplicity.

Figure 9:
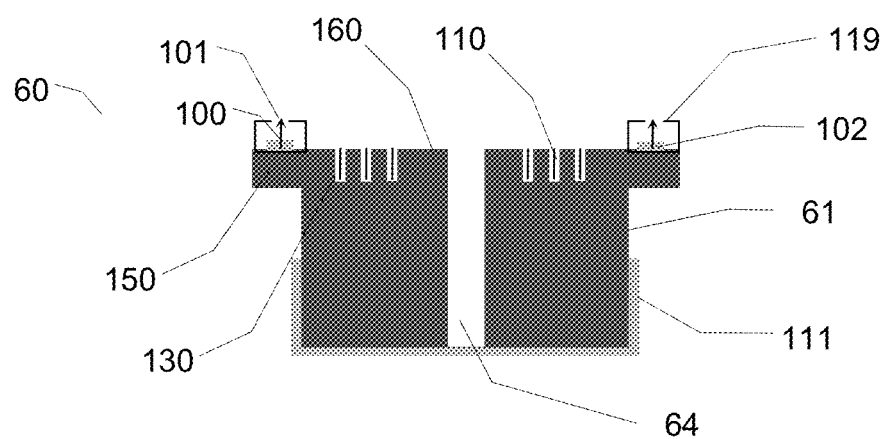
FIG. 9 shows schematic cross-sectional front view of an embodiment of the staple cartridge of the present invention.

In the embodiment shown in FIG. 9, a collapsible protector 119 is at least partially surrounding microneedles 100 disposed on staple cartridge 60 to prevent microneedle 100 damage prior to closing of the jaws of the surgical stapler and insertion of microneedles 100 into the tissue. Collapsible protector 119 can be in a form of a thin collapsible metallic shape, or can be made of easily compressible foam.

Figure 10:
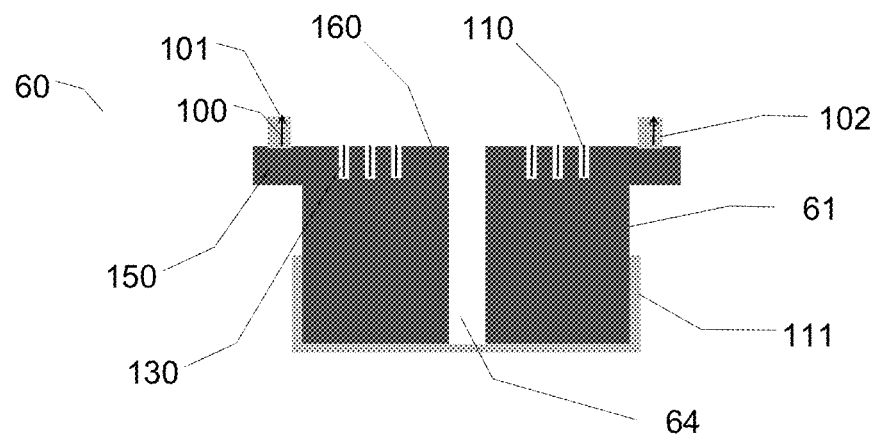
FIG. 10 shows schematic cross-sectional front view of an embodiment of the staple cartridge of the present invention.

In the embodiment shown in FIG. 10, attachment strip 102 is made of thick collapsible material, such as a foam or non-woven felt, and is sized to completely encapsulate and envelop microneedles 100 disposed on staple cartridge 60, thus acting similarly to collapsible protector 119 described supra, to prevent microneedle 100 damage prior to closing of the jaws of the surgical stapler and insertion of microneedles 100 into the tissue. Microneedles 100 are releasably supported within the foam of the attachment strip 102, and are released upon compression of attachment strip 102, insertion of microneedles into the tissue and engagement of barbs 101 with the tissue, while attachment strip 102 is removed with the staple cartridge 60 upon completion of the stapling.

Figure 11:
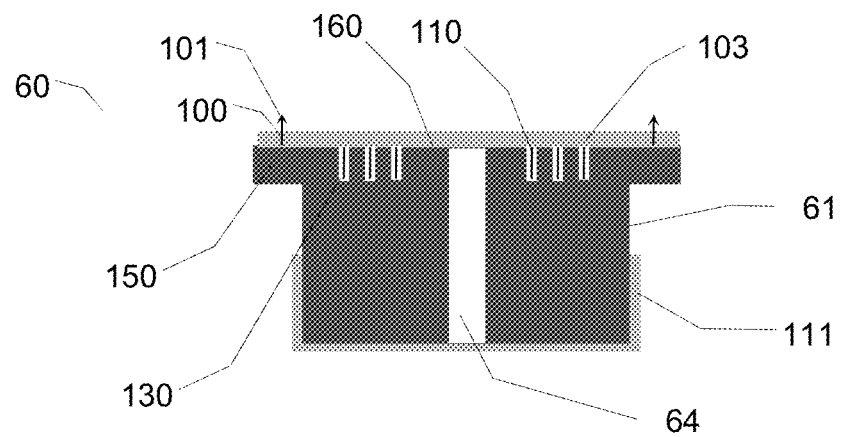
FIG. 11 shows schematic cross-sectional front view of an embodiment of the staple cartridge of the present invention.

In the embodiment shown in FIG. 11, a buttress 103 disposed on the tissue facing surface 160 of staple cartridge 60 is supporting microneedles 100. In this embodiment, microneedles 100 are configured not to separate from buttress 103 upon deployment of microneedles 100 in the tissue. Microneedles 100 are permanently attached to buttress 103 using adhesives, co-molding, welding, insertion, and other methods known to these skilled in the art. In one embodiment, microneedles 100 have optional barbs 101 at the ends distal to tissue facing surface 160, as shown in FIG. 11. In alternative embodiments, microneedles 100 have no barbs 101 as microneedles 100 are supported in the tissue by the buttress 103. Buttress 103 is a thin flat supporting structure made of non-absorbable or preferably absorbable material, such as a synthetic or natural polymer, in a form of woven, non-woven, foam, or molded structure.

In one aspect, buttress 103 covers all tissue facing surface 160 or at least most of the tissue facing surface 160. Use of buttresses and various materials useful for making a buttress are known to these skilled in the arts of surgical stapling. Upon deployment of staples, buttress 103 is attached to tissue layers that are joined by the deployed staples which also penetrate buttress 103 as known in the art. U.S. Pat. No. 6,273,897 "Surgical buttress and surgical stapling apparatus" and U.S. Pat. No. 6,325,810 "Foam buttress for stapling apparatus", both assigned to Ethicon, Inc., describing surgical staplers and buttresses are incorporated by reference herein in their entirety for all purposes.

Figure 12:
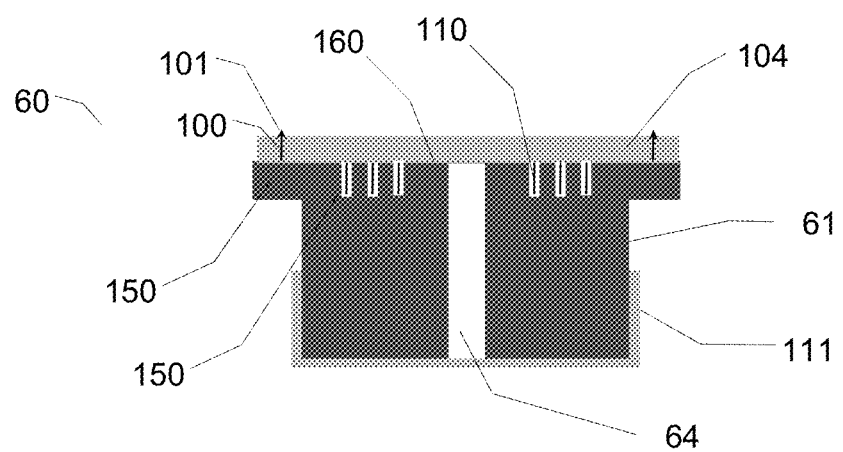
FIG. 12 shows schematic cross-sectional front view of an embodiment of the staple cartridge of the present invention.

In the embodiment shown in FIG. 12, a compressible tissue thickness compensator 104 disposed on the tissue facing surface 160 of staple cartridge 60 supports microneedles 100. In this embodiment, microneedles 100 are configured to be partially, fully, or substantially fully enclosed by the tissue thickness compensator 104 as shown, and are configured not to separate from the compressible tissue thickness compensator 104 upon deployment of microneedles 100 into the tissue. Microneedles 100 are disposed within and are enveloped by the compressible tissue thickness compensator 104. In one embodiment, microneedles 100 have optional barbs 101 at the ends distal to tissue facing surface 160, as shown in FIG. 12. In alternative embodiments, microneedles 100 have no barbs 101 as microneedles 100 are supported in the tissue by the compressible tissue thickness compensator 104. Tissue thickness compensator 104 is a flat supporting structure made of non-absorbable or preferably absorbable material, such as a synthetic or natural polymer, in a form of woven, non-woven, foam, or molded structure. In one aspect, tissue thickness compensator 104 covers all tissue facing surface 160 or at least most of the tissue facing surface 160. Upon deployment of staples tissue thickness compensator 104 is attached to tissue layers that are joined by the deployed staples which also penetrate tissue thickness compensator 104 as known in the art. Use of compressible tissue thickness compensators and various materials useful for making compressible tissue thickness compensators, such as foams and fabrics are known to these skilled in the arts of surgical stapling. U.S. Pat. No. 8,657,176 "Tissue thickness compensator for a surgical stapler", published US Patent Application No. 2012/0241505 "Tissue thickness compensators for circular surgical staplers", and US Patent Application NO. 2012/0241503 "Tissue thickness compensators", describing surgical staplers and compressible tissue thickness compensators, all of which are incorporated by reference herein in their entirety for all purposes.

As will be illustrated below, in the embodiments of the present invention shown in FIGS. 4-12, microneedles 100 are deployed as jaws of the stapler close, i.e. prior to the deployment of staples and stapling of the tissue layers together and prior to deployment of knife cutting surface 45 and staples 110, i.e. prior to stapling of tissue layers together.

Figure 13:
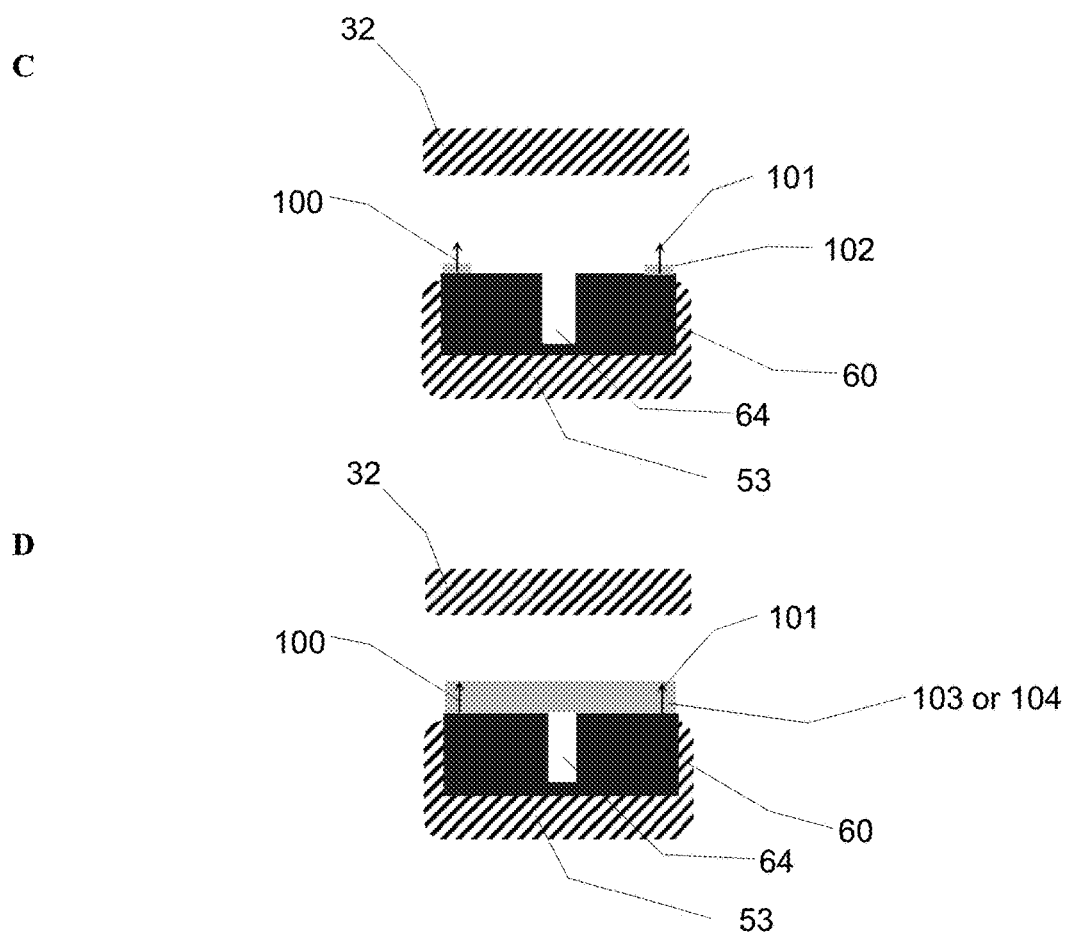
FIG. 13 shows schematic cross-sectional side views and front views of a portion of linear surgical stapler of the present invention in operation.

Referring now to FIG. 13, a portion of linear surgical stapler 20 is shown in a schematic cross-sectional side view, with open upper jaw 32 and lower jaw 53, and staple cartridge 60 installed within lower jaw 53. For simplification, longitudinal slots 63, staples 110, longitudinal channels 130, staple advancers 120, lateral extension 150, and rear cover 111 are not shown in FIG. 13.

FIG. 13A shows staple cartridge 60 with attachment strip 102 and microneedles 100 disposed on attachment strip 102 with tips with optional barbs 101 facing upper jaw 32.

FIG. 13B shows staple cartridge 60 with buttress 103 or with tissue thickness compensator 104 and microneedles 100 disposed on buttress 103 or within tissue thickness compensator 104 with tips with optional barbs 101 facing upper jaw 32.

Referring now to FIGS. 13C and 13D, schematic front cross-sectional views of embodiments shown in FIGS. 13A and 13B are shown, with the view taken from the direction as indicated by arrows in FIGS. 13A and 13B. A schematic cross-sectional front view shows open upper jaw 32 and lower jaw 53, and staple cartridge 60 installed within lower jaw 53.

Staple cartridge 60 with attachment strip 102 and microneedles 100 disposed on attachment strip 102 with tips with optional barbs 101 facing upper jaw 32 is shown in FIG. 13C. Staple cartridge 60 with buttress 103 or with tissue thickness compensator 104 and microneedles 100 disposed on buttress 103 or on tissue thickness compensator 104 with tips with optional barbs 101 facing upper jaw 32 is shown in FIG. 13D.

Figure 14:
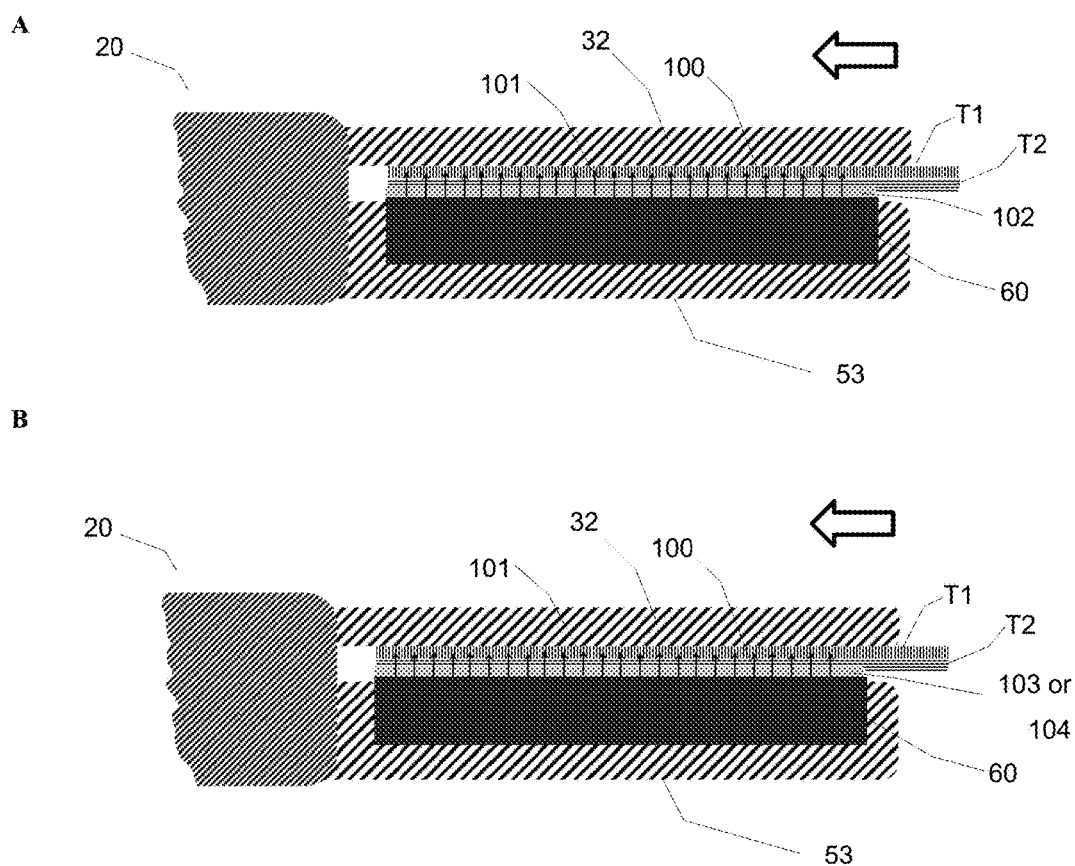
FIG. 14 shows schematic cross-sectional side views and front views of a portion of linear surgical stapler of the present invention in operation.
Figure 14:
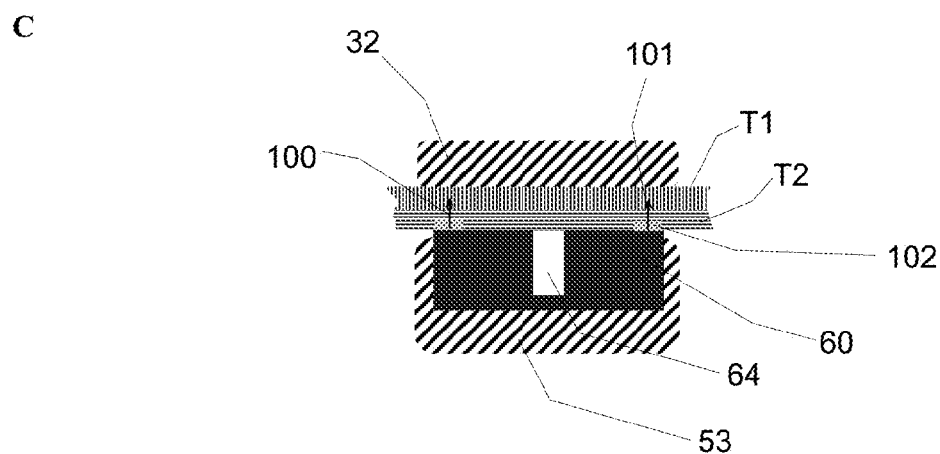
Figure 14:
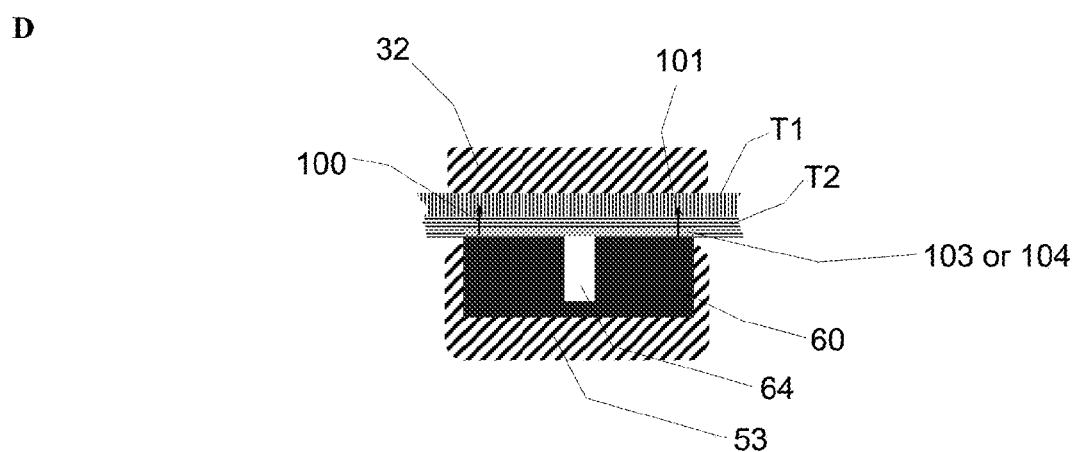

Referring now to FIG. 14, embodiments of a portion of linear surgical stapler 20 as presented in FIG. 13 are shown in a schematic cross-sectional side view, with upper jaw 32 and lower jaw 53 closed onto two layers of tissue T1 and T2 being joined, prior to deployment of staples (staples are not shown in FIG. 14). For simplification, longitudinal slots 63, staples 110, longitudinal channels 130, staple advancers 120, lateral extension 150, and rear cover 111 are not shown in FIG. 14.

FIG. 14A shows staple cartridge 60 with attachment strip 102 and microneedles 100 disposed on attachment strip 102 with tips with optional barbs 101 facing upper jaw 32, showing microneedles 100 entering both layers of tissue T1 and T2.

FIG. 14B shows staple cartridge 60 with microneedles 100 disposed on buttress 103 or within tissue thickness compensator 104 with tips with optional barbs 101 facing upper jaw 32, showing microneedles 100 entering both layers of tissue T1 and T2.

Advantageously, because microneedles 100 in the embodiments of FIGS. 11, 12, 13B, 14B are supported on the tissue by buttress 103 or tissue thickness compensator 104, the barbs 101 are optional. In one aspect of these embodiments, microneedles 100 have no barbs (not shown).

Referring now to FIGS. 14C and 14D, schematic front cross-sectional views of embodiments shown in FIGS. 14A and 14B are shown, with the view taken from the direction as indicated by arrows in FIGS. 14A and 14B, similar to FIGS. 13A-D. A schematic cross-sectional front view shows upper jaw 32 and lower jaw 53 closed onto two layers of tissue T1 and T2 being joined, prior to deployment of staples (staples are not shown in FIG. 14).

Staple cartridge 60 with attachment strip 102 and microneedles 100 disposed on attachment strip 102 with tips with optional barbs 101 facing upper jaw 32 is shown in FIG. 13C. Staple cartridge 60 with buttress 103 or with tissue thickness compensator 104 and microneedles 100 disposed on buttress 103 or on tissue thickness compensator 104 with tips with optional barbs 101 facing upper jaw 32 is shown in FIG. 13D.

It is to be understood, that after closing of upper jaw 32 and lower jaw 53 onto layers of tissue T1 and T2, microneedles 100 will be inserted into tissue by the force of the jaws 32 and 53 compressing tissue layers T1 and T2 between said jaws. Thereafter the staples are fired into the tissue layers T1 and T2 forming a stapled tissue joint, as it is known in the art. Sharp tips of microneedles 100 facilitate piercing of tissue layers T1 and T2 by microneedles 100. Optional barbs 101 prevent microneedles 100 from exiting stapled tissue layers T1 and T2. Advantageously, because microneedles 100 in the embodiments of FIGS. 11, 12, 13B, 14B are supported on the tissue by buttress 103 or tissue thickness compensator 104, the barbs 101 are optional in these embodiments. Accordingly, in some aspects of the present invention, there are no barbs on microneedles.

Figure 15:
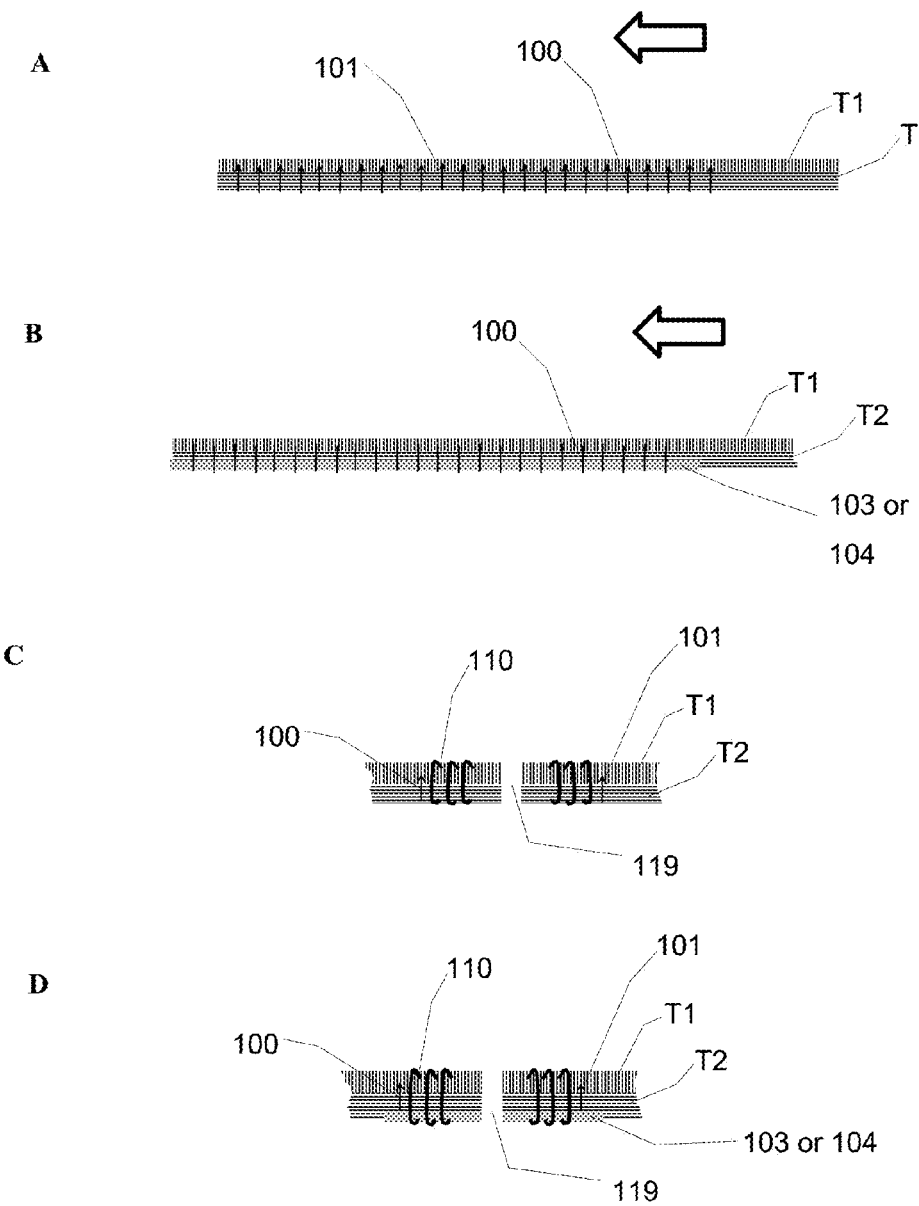
FIG. 15 shows simplified cross-sectional view of joined tissue layers according to embodiments of the present invention.

Referring now to FIG. 15, joined tissue layers are shown after stapling, resection, and removal of surgical stapler in a simplified cross-sectional view. FIG. 15A shows joined tissue layers T1 and T2 whereby microneedles 100 have separated from attachment strip 102 (not shown in FIG. 15), whereby microneedles 100 have entered both layers of tissue T1 and T2. Barbs 101 prevent microneedles 100 from exiting stapled tissue layers T1 and T2. Staples 110 are not shown.

FIG. 15B shows joined tissue layers T1 and T2 whereby microneedles 100 are supported on buttress 103 or tissue thickness compensator 104 and have entered both layers of tissue T1 and T2. In this embodiment barbs 101 are optional and are not shown in FIG. 15B. Staples 110 are not shown.

FIG. 15C shows schematic front cross-sectional view of embodiment shown in FIG. 15A, with the view taken from the direction as indicated by arrow in FIG. 15A. Tissue layers T1 and T2 joined by three rows of staples 110 on each side of the resection line 119 separating tissue into two parts are shown, with microneedles 100 positioned outside of the stapled area and distal to the resection line 119 shown entered both layers of tissue T1 and T2.

FIG. 15D shows schematic front cross-sectional view of embodiment shown in FIG. 15B, with the view taken from the direction as indicated by arrow in FIG. 15B. Tissue layers T1 and T2 joined by three rows of staples 110 on each side of the resection line 119 are shown, with microneedles 100 positioned outside of the stapled area and distal to the resection line 119. Microneedles 100 are supported on buttress 103 or tissue thickness compensator 104 and are shown entered both layers of tissue T1 and T2. Buttress 103 or tissue thickness compensator 104 are shown attached to the joined tissue layers T1 and T2 by three rows of staples 110 on each side of the resection line 119, with resection line 119 also separating buttress 103 or tissue thickness compensator 104 into two parts.

Microneedles 100 are shown in FIG. 15 entering both layers of the tissue T1 and T2 and configured to remain in both layers of tissue after stapling, outside of the compressed and stapled areas of tissue, outside of the staple lines and distal to the tissue resection line.

Figure 16:
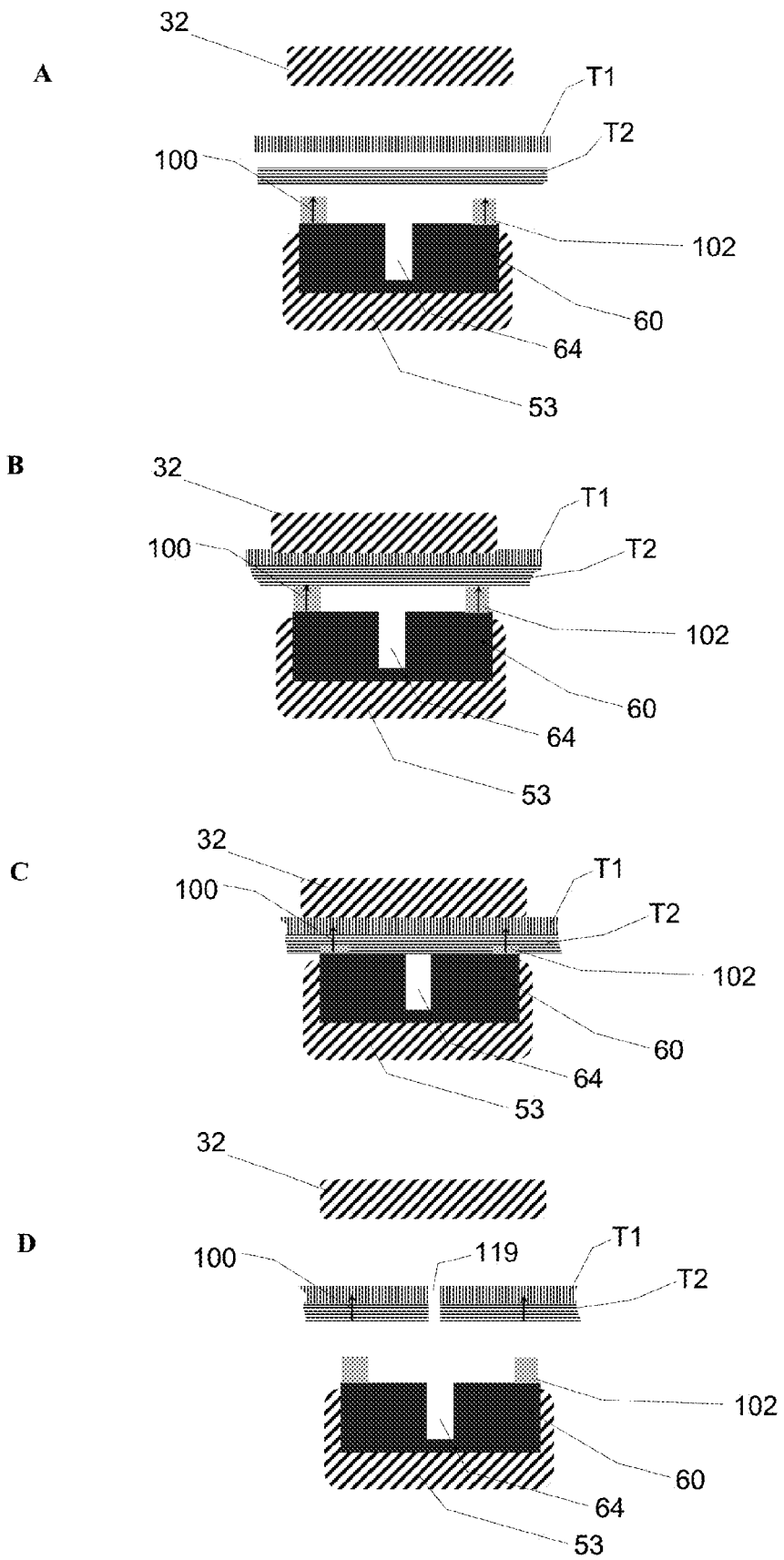
FIG. 16 shows sequence of stapling tissue layers in a schematic frontal cross-sectional view.

Referring now to FIG. 16, sequence of stapling tissue layers T1 and T2 is shown in a schematic frontal cross-sectional view similar to FIGS. 13C, 14C, 15C, with attachment strip 102 made of thick compressible or collapsible material, such as a foam, and is sized to partially or completely encapsulate and envelop microneedles 100, similar to embodiment of FIG. 10. Staples 110 are not shown in FIG. 16 for simplification.

FIG. 16A shows upper jaw 32 and lower jaw 53 open with tissue layers T1 and T2 between upper jaw 32 and lower jaw 53, with microneedles 100 releasably supported within the foam of the attachment strip 102 which is supported on staple cartridge 60 having slot 64.

FIG. 16B shows the start of the compression of tissue layers T1 and T2 between jaws 32 and 53, with tissue layers T1 and T2 in initial contact with upper jaw 32 and microneedles 100 and the foam of the attachment strip 102.

FIG. 16C shows compression of tissue layers T1 and T2 between jaws 32 and 53, whereby attachment strip 102 is shown also compressed releasing microneedles 100 that are entering tissue layers T1 and T2.

FIG. 16D shows that upon insertion of the microneedles 100 into tissue, firing of the staples (not shown), upper jaw 32 and lower jaw 53 are opened releasing now joined tissue layers T1 and T2 with microneedles 100 in the tissue and separated from attachment strip 102. Staple cartridge 60 with still attached now expanded attachment strip 102 is supported on lower jaw 53 and is not in contact with tissue. Resection line 119 is shown separating tissue into two parts.

Figure 17:
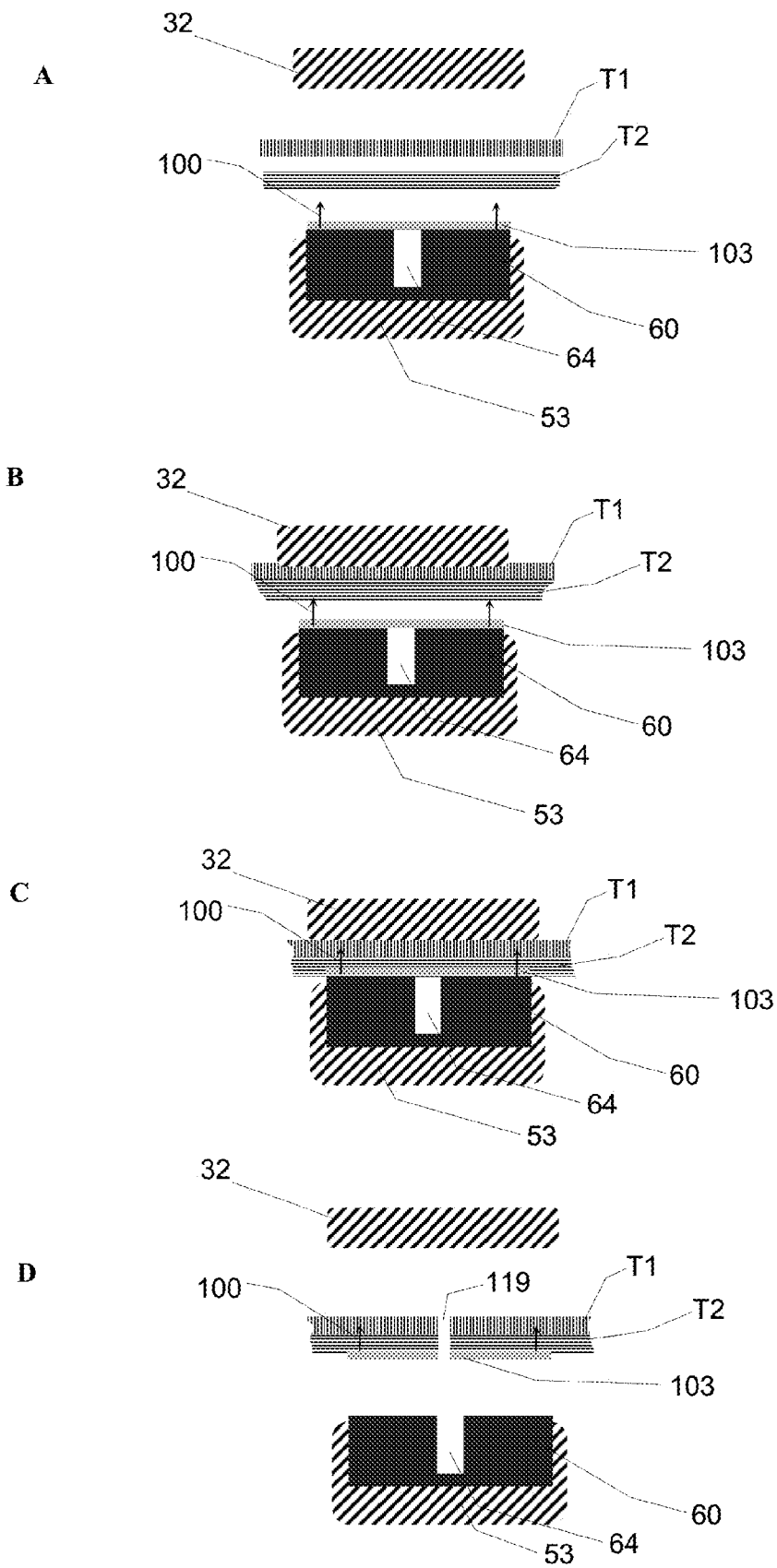
FIG. 17 shows sequence of stapling tissue layers in a schematic frontal cross-sectional view.

Referring now to FIG. 17, sequence of stapling tissue layers T1 and T2 is shown in a schematic frontal cross-sectional view similar to FIGS. 13D, 14D, 15D, with microneedles 100 supported on thin buttress 103, similar to embodiment of FIG. 11. Staples 110 are not shown in FIG. 17 for simplification.

FIG. 17A shows upper jaw 32 and lower jaw 53 open with tissue layers T1 and T2 between upper jaw 32 and lower jaw 53, with microneedles 100 permanently supported on buttress 103 which is releasably supported on staple cartridge 60 having slot 64.

FIG. 17B shows the start of the compression of tissue layers T1 and T2 between jaws 32 and 53, with tissue layers T1 and T2 in first contact with microneedles 100 and upper jaw 32.

FIG. 17C shows compression of tissue layers T1 and T2 between jaws 32 and 53, whereby microneedles 100 are entering tissue layers T1 and T2.

FIG. 17D shows that upon insertion of the microneedles 100 into tissue, firing of the staples (not shown), upper jaw 32 and lower jaw 53 are opened releasing now joined tissue layers T1 and T2 with microneedles 100 supported in the tissue on buttress 103 which has now separated from staple cartridge 60. Buttress 103 is attached to tissue with staples (not shown) fired from staple cartridge 60. Resection line 119 is shown separating buttress 103 and tissue into two parts.

Figure 18:
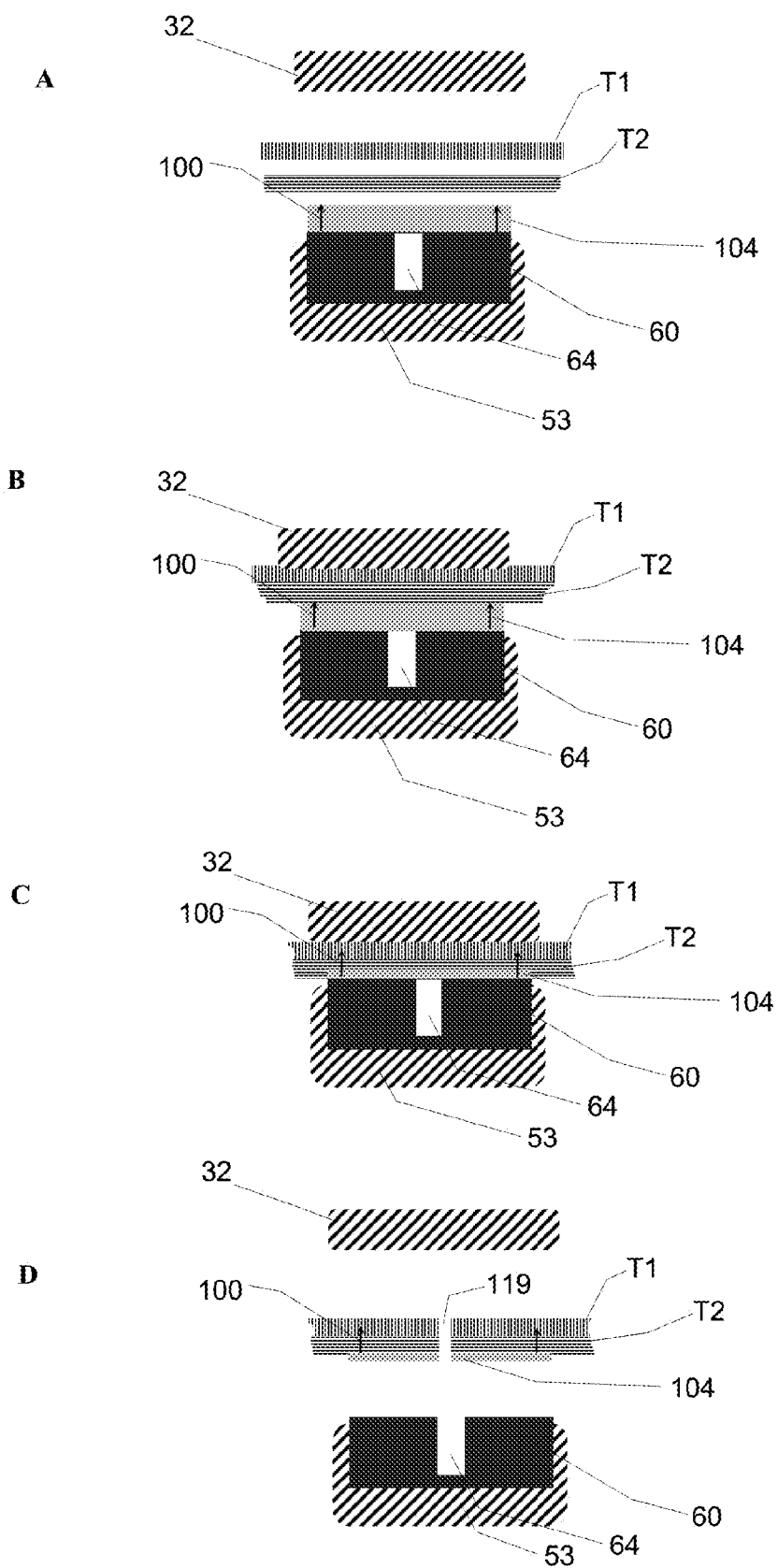
FIG. 18 shows sequence of stapling tissue layers in a schematic frontal cross-sectional view.

Referring now to FIG. 18, sequence of stapling tissue layers T1 and T2 is shown in a schematic frontal cross-sectional view similar to FIGS. 13D, 14D, 15D, with tissue thickness compensator 104, similar to embodiment of FIG. 12. Staples 110 are not shown in FIG. 18 for simplification.

FIG. 18A shows upper jaw 32 and lower jaw 53 open with tissue layers T1 and T2 between upper jaw 32 and lower jaw 53, with microneedles 100 permanently supported on tissue thickness compensator 104 which is releasably supported on staple cartridge 60 having slot 64.

FIG. 18B shows the start of the compression of tissue layers T1 and T2 between jaws 32 and 53, with tissue layers T1 and T2 in initial contact with upper jaw 32 and microneedles 100 and/or with tissue thickness compensator 104.

FIG. 18C shows compression of tissue layers T1 and T2 between jaws 32 and 53, whereby microneedles 100 are entering tissue layers T1 and T2 and tissue thickness compensator 104 compresses.

FIG. 18D shows that upon insertion of the microneedles 100 into tissue, firing of the staples (not shown), upper jaw 32 and lower jaw 53 are opened releasing now joined tissue layers T1 and T2 with microneedles 100 supported in the tissue on tissue thickness compensator 104 which has separated from staple cartridge 60. Tissue thickness compensator 104 is attached to tissue with staples (not shown) fired from staple cartridge 60. Resection line 119 is shown separating tissue thickness compensator 104 and tissue into two parts.

According to alternative embodiments of the present invention, microneedles 100 are disposed on the upper jaw 32 facing the tissue.

Barbed and non-barbed microneedles can be manufactured by a variety of techniques known to a skilled artisan, including injection molding, laser cutting, casting, 3D printing, micromachining, embossing, and other known techniques. Microneedles can also be made of a rigid extruded monofilament, cut under angle for sharpness, and optionally barbed by partial surface cutting. In one aspect, semi-rigid extruded monofilament has barbs typical of a barbed suture, with a plurality of barbs present on the microneedle made of extruded monofilament. The strength and dimensional stability of the microneedles are sufficient to penetrate into the tissue without breakage.

Material of construction of the microneedles is any soluble and/or absorbable polymer, synthetic, or natural, and combinations thereof, including, but not limited to, polyesters and/or co-polyesters based on monomers such as lactide, glycolide, p-dioxanone, and combinations thereof; polyvinyl alcohol; gelatin; collagen; fibrin; and combinations thereof; or any other biocompatible, bioabsorbable polymers known to a skilled artisan. In all embodiments, the microneedles are intended to fully absorb into the surrounding tissue within the time period relevant to the wound healing or somewhat longer than the wound healing, i.e. within periods of from about a 1 day to 2-3 days to 1-3 weeks to about 8-10 weeks.

According to embodiments of the present invention, microneedles 100 or 100a are from about 50 microns to about 1500 microns in diameter, more preferably from 100 to 1000 microns, such as 200 or 500 microns. According to embodiments of the present invention, microneedles 100 or 100a are from about 100 microns to about 3000 microns long, such as 500 microns or 1000 microns or 2000 microns long. In certain embodiments, there are from about 10 to about 500 or 1000 microneedles, more preferably at least 10 microneedles, most preferably at least 25 or 50 or 100 microneedles arranged in one or several microneedle arrays or groups.

Figure 19:
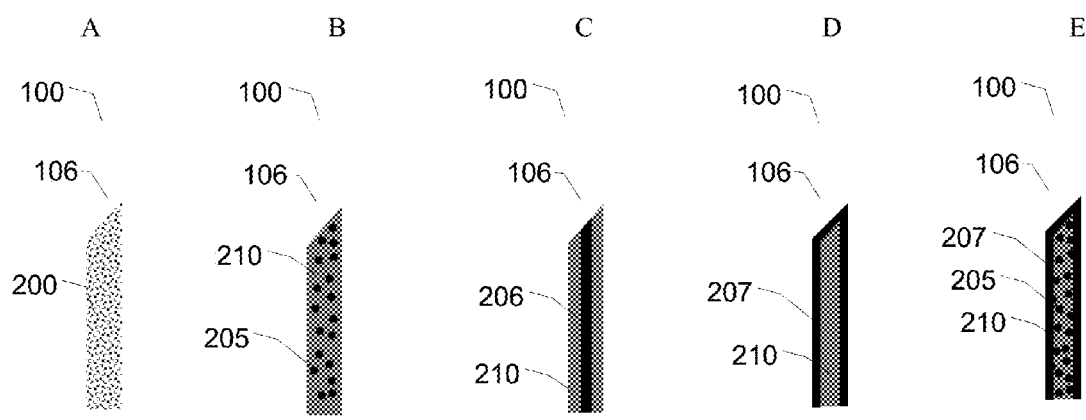
FIG. 19 shows schematic cross-sectional side views of microneedles of the present invention.

Referring now to FIG. 19, microneedles 100 without barbs are shown, having sharpened tips 106. The microneedles 100 can be barb-less as shown, or have barbs which are not shown for simplicity. FIG. 19A shows absorbable microneedle 100 with medicant 200 distributed throughout the microneedle body. The microneedle of FIG. 19A is made of absorbable polymeric material impregnated with the medicant 200. The medicant can be compounded into the polymer, or the microneedle can be exposed to the medicant or the medicant in a carrier solution resulting in penetration and diffusion of the medicant into the microneedle.

FIG. 19B shows absorbable microneedle 100 with medicant in the form of discrete particles or micro-beads or microspheres 205 distributed within polymer 210 comprising microneedle 100 body.

FIG. 19C shows absorbable microneedle 100 with medicant in the form of discrete elongated insert 206 within polymer 210 comprising microneedle 100 body.

FIG. 19D shows absorbable microneedle 100 with medicant in the form of coating 207 coated on the outside of microneedle 100.

FIG. 19E shows absorbable microneedle 100 with medicant in the form of coating 207 coated on the outside of microneedle 100, with the same or different medicant in the form of discrete particles or micro-beads or microspheres 205 distributed within polymer 210 comprising microneedle 100 body. In this embodiment, the medicant in the coating 207 is released first, in the time frame immediately following the insertion of microneedles 100, i.e. over time of a few hours, such as 1 hour, 5 hours, 12 hours, 24 hours, or similar, and whereby the medicant in the form of discrete particles 205 is released over time, i.e. within one or several days or weeks, such as 3 days, 1 week, 2 weeks, 3 weeks, or similar.

In microneedles of the present invention, medicant 200 is released from the microneedles 100 by a variety of mechanisms, i.e. by diffusing out of the microneedle, by release due to the dissolution and/or absorption of the microneedle into the body, or by both mechanisms.

In some embodiments, the medicant is released faster than the full resorption of the microneedle. In one aspect, the medicant is released over 1, 2, or 3 days, while full resorption/dissolution of the microneedle is occurring over 1, 2, or 3 weeks. In another aspect, the medicant is released over 1, 2, or 3 weeks, while full resorption/dissolution of the microneedle is occurring over 3, 5, or 8 weeks. In alternative embodiments, the medicant is released substantially synchronously with the resorption of the microneedle, i.e. the medicant is released over about the same time as the resorption of the microneedle is progressing.

In further alternative embodiments, the medicant is released slower than the dissolution of the microneedle. In one aspect, the microneedle dissolves within 1, 2, or 7 days, while micro particles of the medicant continue releasing the medicant over 1, 2, or 3 weeks.

Figure 20:
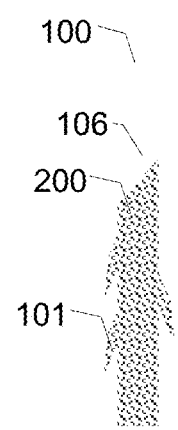
FIG. 20 shows schematic cross-sectional side view of microneedle of the present invention.

Referring now to FIG. 20, microneedle 100 with multiple barbs 101 is shown, with barbs 101 positioned along the microneedle 100 length. Absorbable microneedle 100 is shown having sharpened tip 106 with medicant 200 distributed throughout the microneedle body. The microneedle 100 of FIG. 20 is a short section of a barbed monofilament, essentially a short section of a barbed suture, and is made of absorbable polymeric material impregnated with the medicant 200. In an alternative embodiment (not shown), microneedle 100 of FIG. 20 is further coated with medicant 200.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A linear surgical stapler for joining tissue layers comprising:
   a) a disposable cartridge installed in a first jaw connected to an opposing second jaw, said cartridge containing a plurality of deployable staples in arrays separated by a tissue resection slot;
   b) a plurality of resorbable medicant-releasing microneedles, said microneedles comprising elongated rods having a sharp tissue-penetrating distal end and a proximal end;
   said microneedles releasably disposed on or within a tissue-facing surface of the cartridge, wherein the proximal end of the microneedles is supported on the cartridge, and wherein said microneedles are releasably supported by an attachment strip disposed on the tissue-facing surface.

2. The stapler of claim 1, wherein the microneedles are positioned on a periphery of the cartridge outside of the arrays of the staples and distally to the tissue resection slot.

3. The stapler of claim 1, wherein said microneedles further comprise a barb at the distal end thereof and wherein said microneedles are substantially perpendicular to the tissue-facing surface.

4. The stapler of claim 1, wherein the attachment strip is a compressible foam layer, and wherein said microneedles are embedded within said compressible foam layer.

5. The stapler of claim 1, wherein said microneedles are supported by a buttress or a tissue thickness compensator releasably disposed on the tissue-facing surface.

6. The stapler of claim 1, wherein said microneedles are configured to be left in the tissue layers after joining of the tissue layers.

7. The stapler of claim 1, wherein said medicant comprises a drug, an enzyme, a growth factor, an anti-inflammatory agent, a vasodilating agent, a peptide, a protein, a nutrient, an excipient, a cell, or combinations thereof.

8. The stapler of claim 1, wherein the medicant is released over a period of from about 2 hours to about 4 weeks, more preferably from about 4 hours to about 5 days, most preferably from about 4 hours to about 3 days.

9. The stapler of claim 1, wherein the cartridge comprises at least 10 microneedles and wherein said microneedles are from 50 microns to about 1000 microns in diameter and from about 100 microns to about 2500 microns long.

10. A method of joining tissue layers using a linear stapler assembly having a plurality of soluble or resorbable microneedles that contain at least one medicant on a disposable cartridge installed in a first jaw connected to an opposing second jaw of a linear stapler, said cartridge containing a plurality of deployable staples in arrays separated by a tissue resection slot wherein said microneedles are elongated rods having a tissue-penetrating distal end and a proximal end that are releasably disposed on or within a tissue-facing surface of the cartridge, wherein the proximal end of the microneedles is supported on the cartridge, wherein said microneedles are releasably supported by an attachment strip disposed on the tissue-facing surface comprising:
   a) positioning at least two tissue layers between the first jaw connected and the second jaw;
   b) bringing the first jaw connected and the second jaw together thus compressing the tissue layers between said jaws;
   c) thus deploying said microneedles into said tissue layers;
   d) simultaneously or consecutively deploying the plurality of staples into the tissue layers thus closing or joining the tissue layers;
   e) opening the jaws and removing the linear stapler with the cartridge from contact with the tissue layers, allowing the microneedles to stay in the tissue layers such that the medicant is released over time into the tissue layers in the vicinity and/or adjacent to the microneedles.

11. The method of claim 10, wherein the microneedles are positioned on a periphery of the cartridge outside of the arrays of the staples and distally to the tissue resection slot.

12. The method of claim 10, wherein said microneedles further comprise a barb at the distal end thereof and wherein said microneedles are substantially perpendicular to the tissue-facing surface.

13. The method of claim 10, wherein the attachment strip is a compressible foam layer, and wherein said microneedles are embedded within said compressible foam layer.

14. The method of claim 10, wherein said microneedles are supported by a buttress or a tissue thickness compensator releasably disposed on the tissue-facing surface.

15. The method of claim 10, wherein said microneedles are configured to separate from the cartridge upon opening of the jaws and removing the linear stapler with the cartridge from contact with the tissue layers, with the microneedles remaining in the tissue layers after joining of the tissue layers, said microneedles fully dissolving or resorbing within the tissue layers over time.

16. The method of claim 10, wherein said medicant comprises a drug, an enzyme, a growth factor, an anti-inflammatory agent, a vasodilating agent, a peptide, a protein, a nutrient, an excipient, a cell, or combinations thereof.

17. The method of claim 10, wherein the medicant is released over a period of from about 2 hours to about 4 weeks, more preferably from about 4 hours to about 5 days, most preferably from about 4 hours to about 3 days.

18. The method of claim 10, wherein the cartridge comprises at least 10 microneedles and wherein said microneedles are from 50 microns to about 1000 microns in diameter and from about 100 microns to about 2500 microns long.

\* \* \* \* \*